United States Patent [19]

Bonutti

[11] Patent Number: 5,782,862
[45] Date of Patent: Jul. 21, 1998

[54] SUTURE ANCHOR INSERTER ASSEMBLY AND METHOD

[76] Inventor: Peter M. Bonutti, 1303 W. Evergreen Plz., Effingham, Ill. 62401

[21] Appl. No.: 673,923

[22] Filed: Jul. 1, 1996

[51] Int. Cl.⁶ .................................................. A61B 17/04
[52] U.S. Cl. .............................. 606/232; 606/104
[58] Field of Search ............................. 606/232, 104

[56] References Cited

U.S. PATENT DOCUMENTS

| | | | |
|---|---|---|---|
| 2,248,054 | 7/1941 | Becker | 606/104 |
| 4,448,194 | 5/1984 | DiGiovanni et al. | 606/232 |
| 5,002,550 | 3/1991 | Li | 606/232 |
| 5,041,129 | 8/1991 | Hayhurst et al. | 606/232 |
| 5,100,417 | 3/1992 | Cerier et al. | 606/232 |
| 5,141,520 | 8/1992 | Goble et al. | 606/232 |
| 5,180,388 | 1/1993 | DiCarlo | 606/104 |
| 5,258,016 | 11/1993 | DiPoto et al. | 606/104 |
| 5,354,298 | 10/1994 | Lee et al. | 606/232 |
| 5,403,348 | 4/1995 | Bonutti | 606/232 |
| 5,411,523 | 5/1995 | Goble | 606/232 |
| 5,464,426 | 11/1995 | Bonutti | 606/232 |
| 5,478,353 | 12/1995 | Yoon | 606/213 |
| 5,522,844 | 6/1996 | Johnson | 606/232 |
| 5,522,846 | 6/1996 | Bonutti | 606/232 |
| 5,662,658 | 9/1997 | Wenstrom, Jr. | 606/104 |

*Primary Examiner*—Gary Jackson
*Attorney, Agent, or Firm*—Tarolli, Sundheim, Covell, Tummino & Szato

[57] ABSTRACT

A suture anchor inserter assembly includes a manually engageable handle and a shaft which extends axially outward from the handle. The shaft includes an inner member which is fixedly connected with the handle and an outer member which is retractable into the handle. An anchor is received in a chamber formed at the outer end of the shaft. A suture extends through a passage in the shaft, a passage in the handle and along an outer side of the shaft. The suture is tensioned to press the anchor into the chamber in the handle. A retainer assembly is manually operable to release the outer member for axial movement relative to the inner member. The handle advantageously has a triangular cross-sectional configuration.

272 Claims, 10 Drawing Sheets

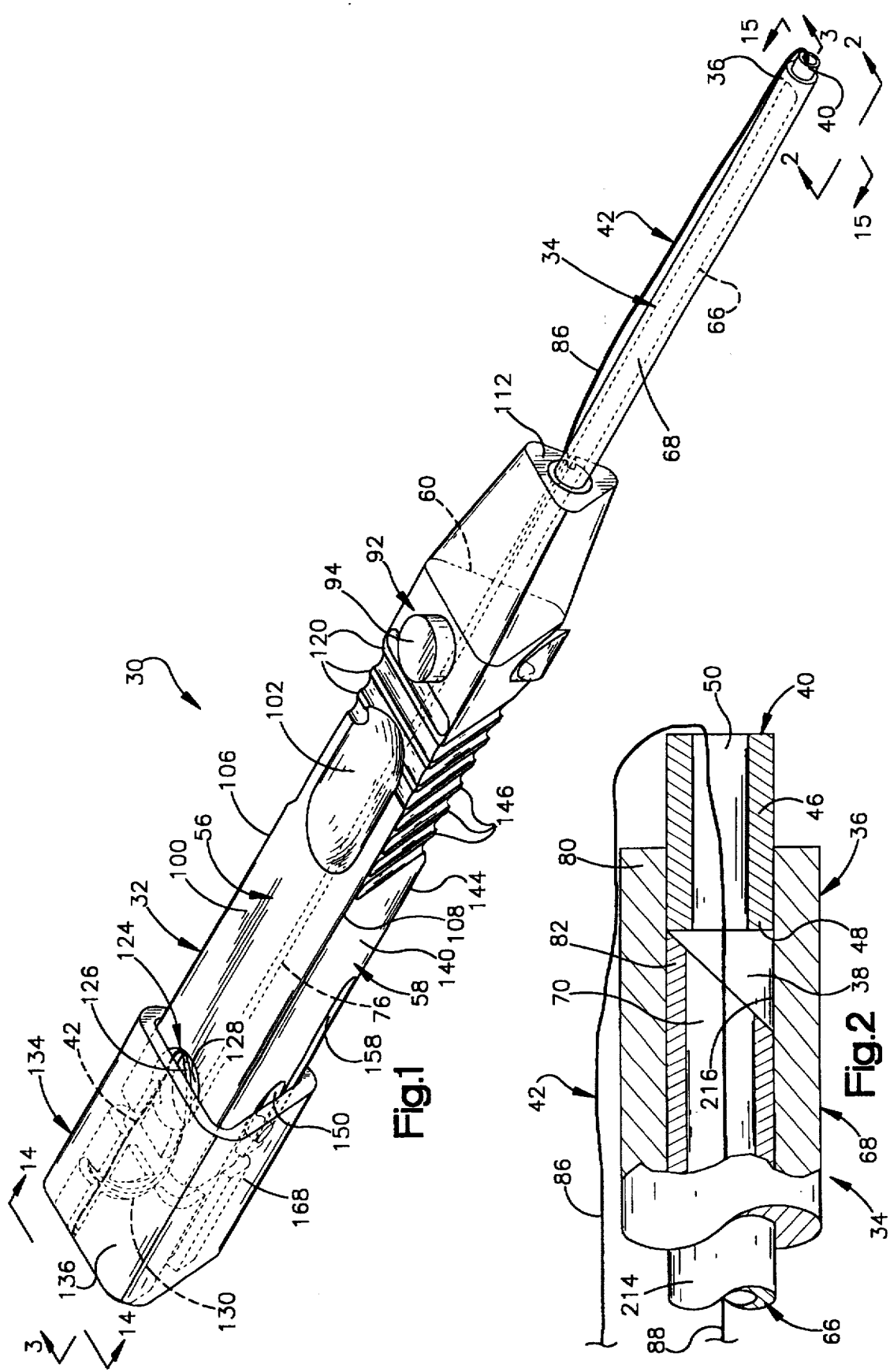

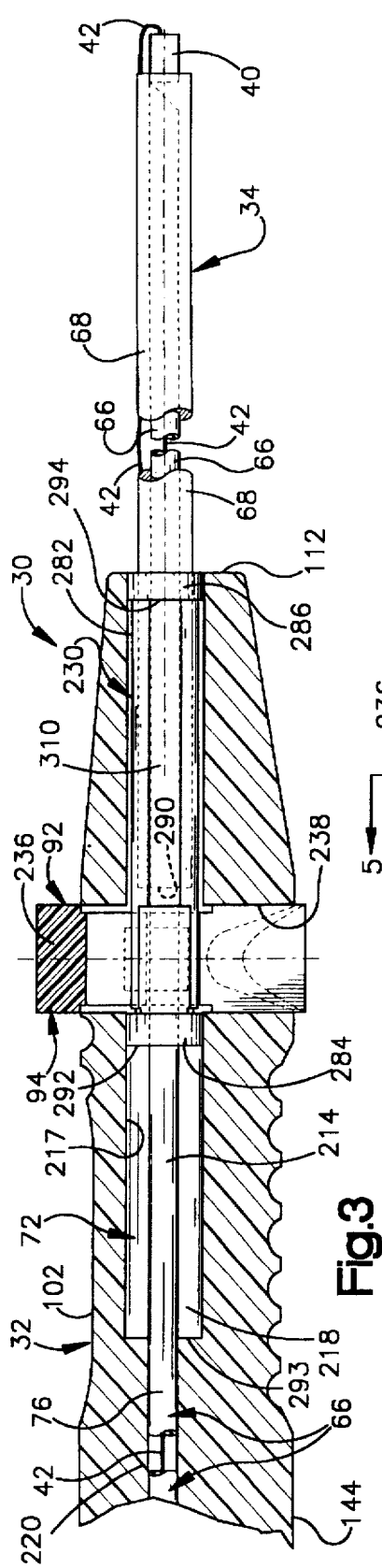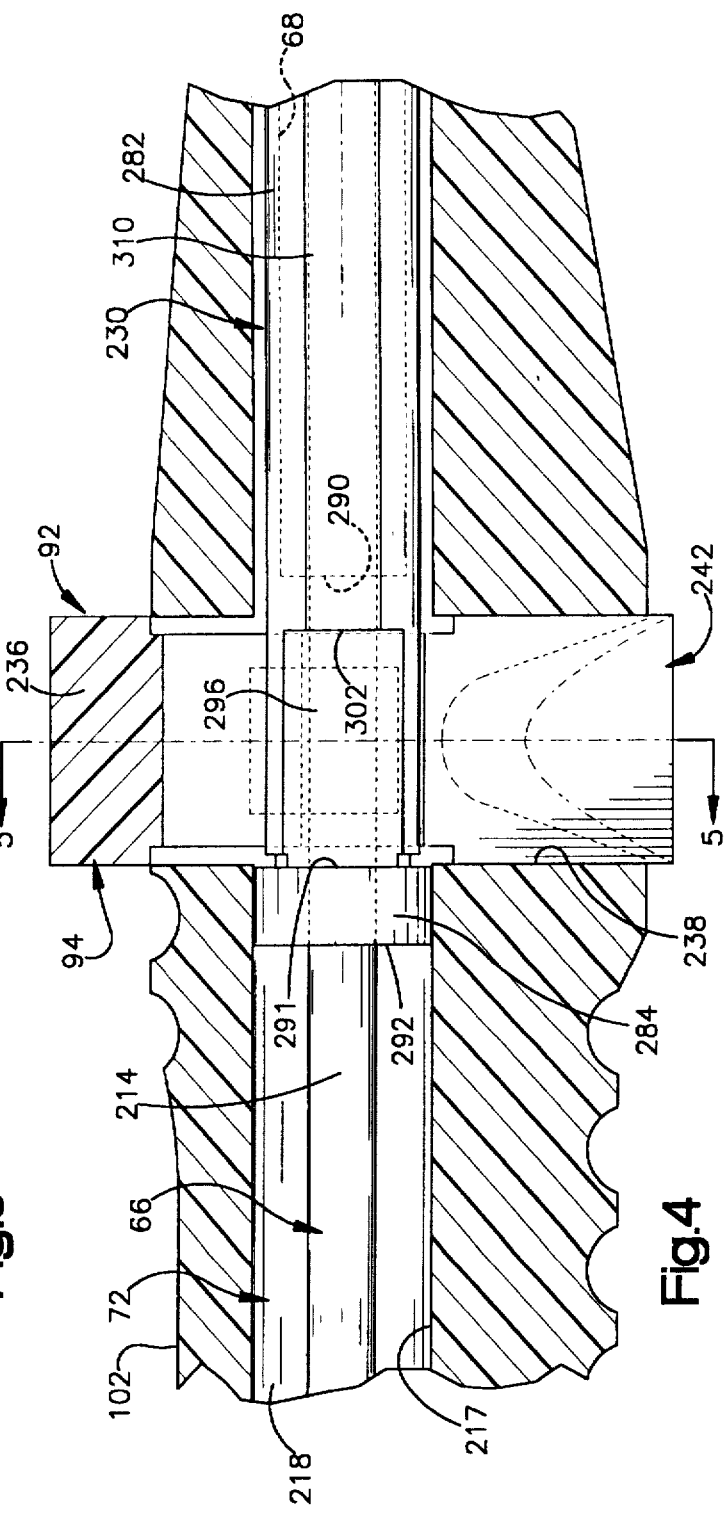

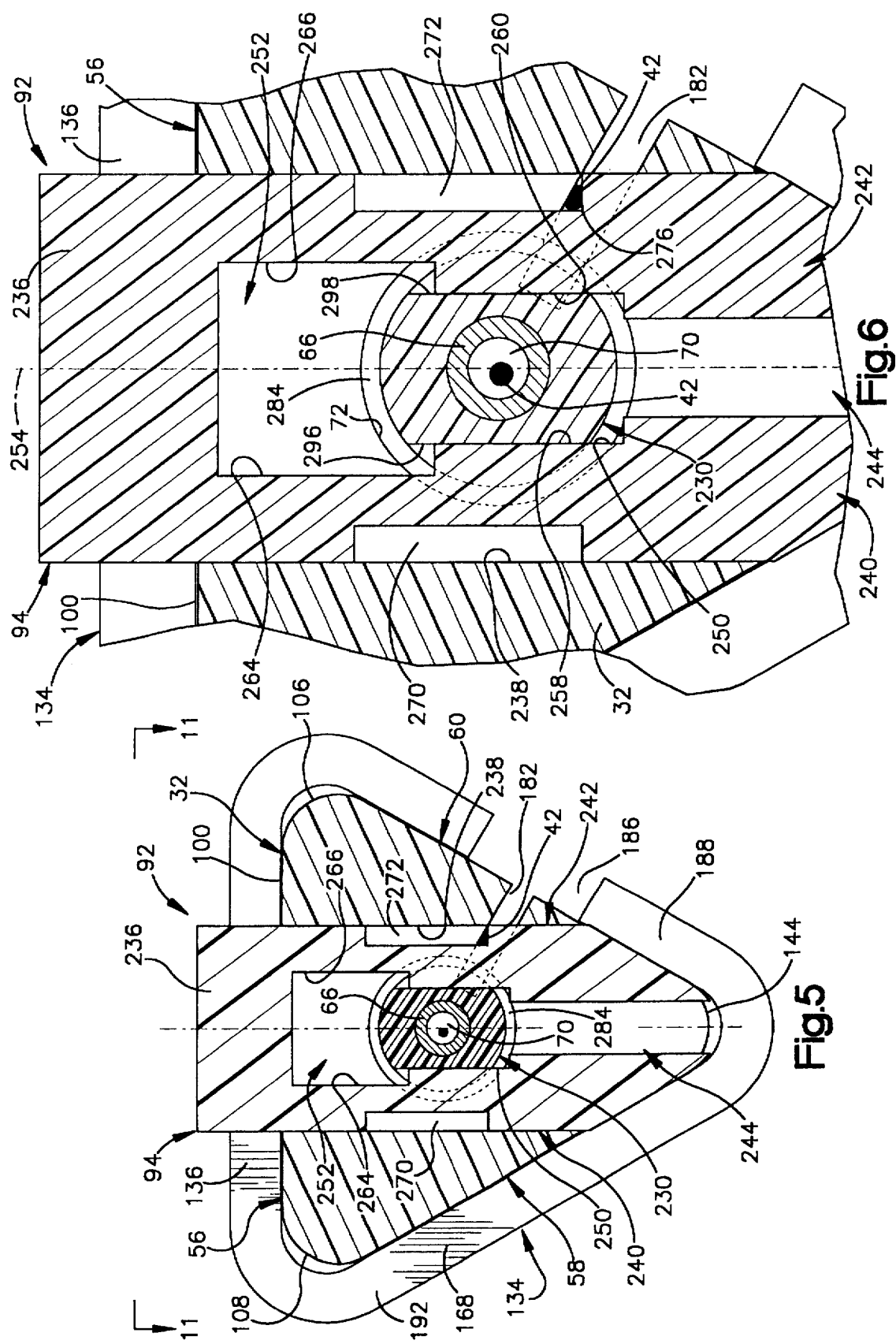

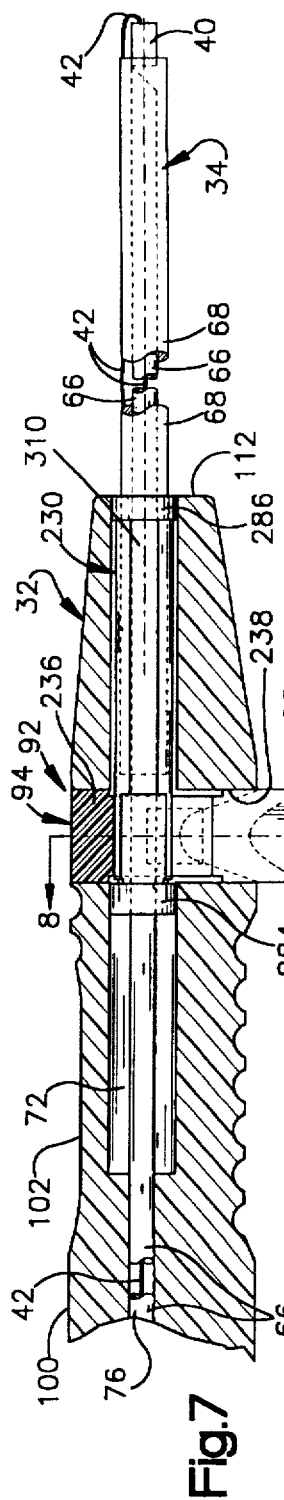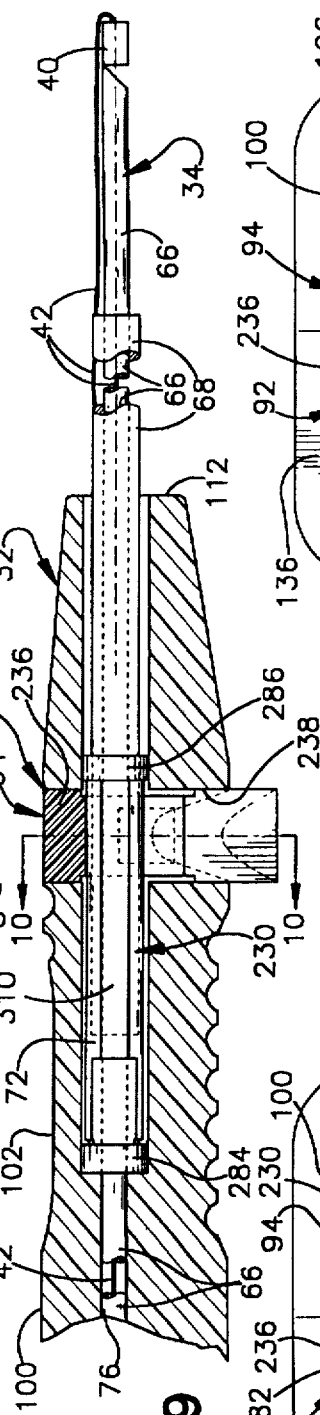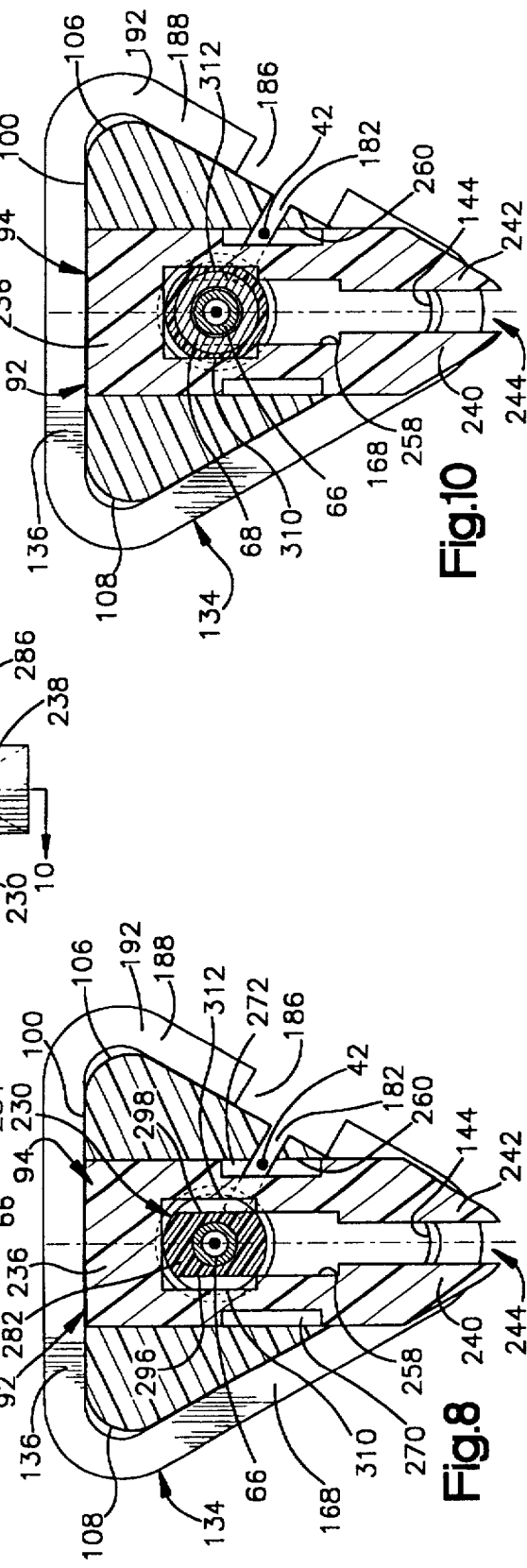

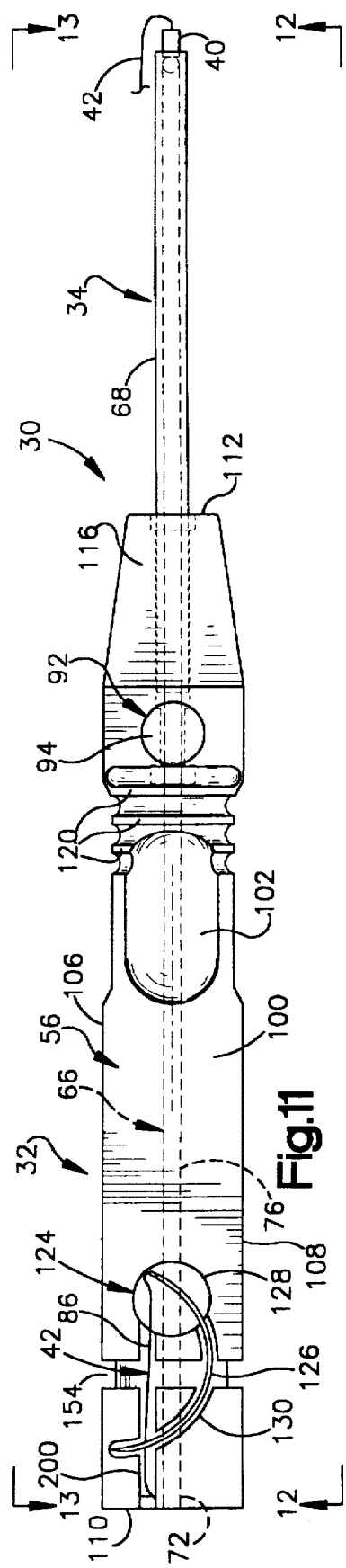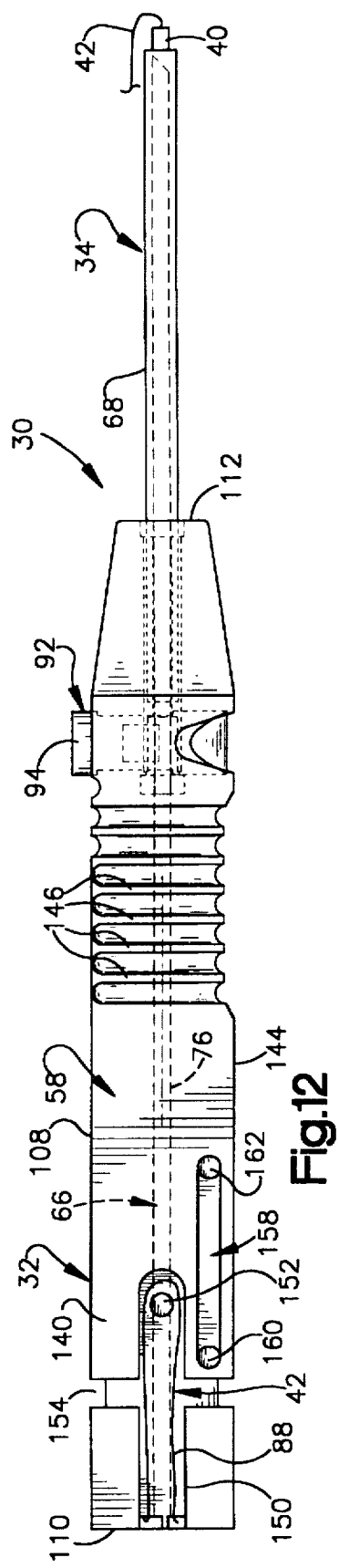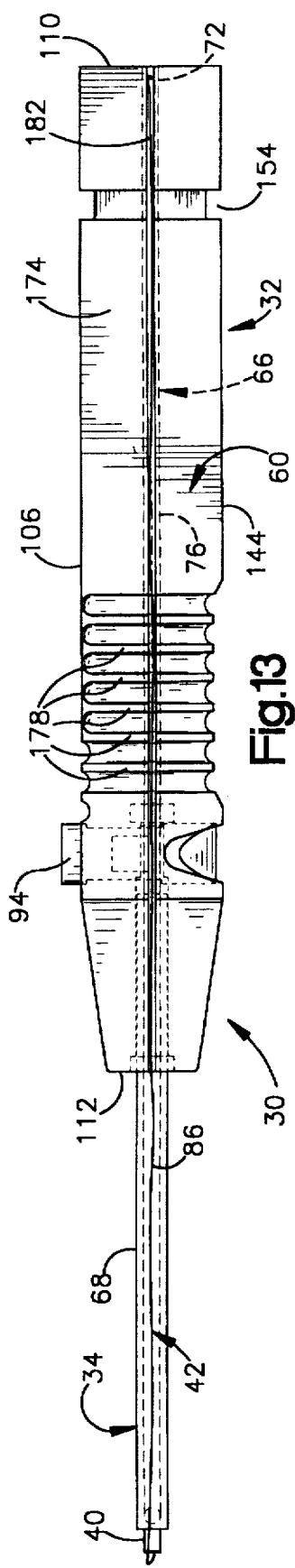

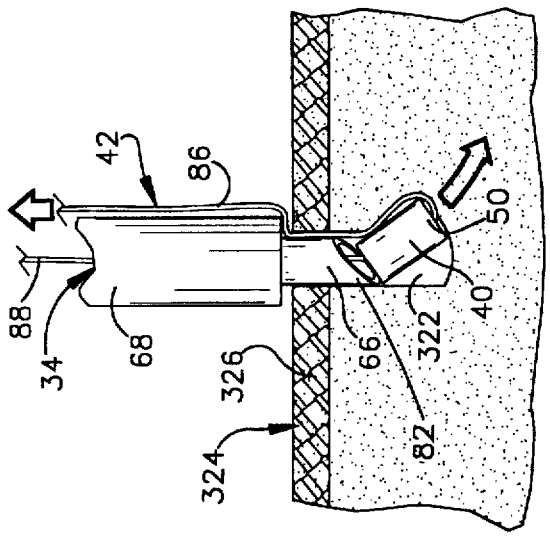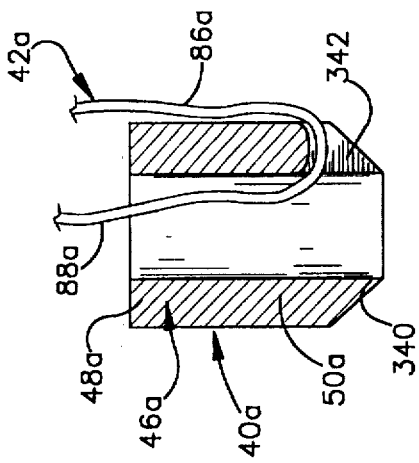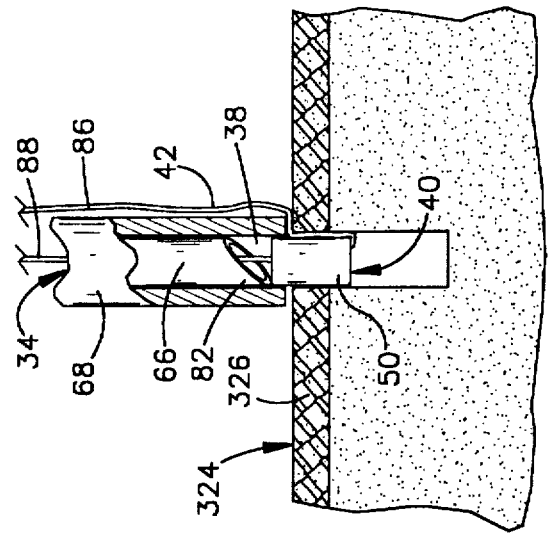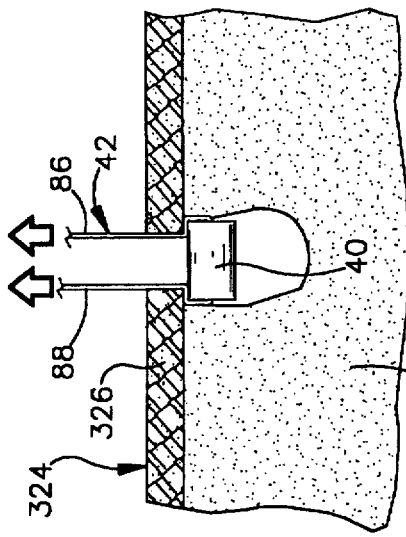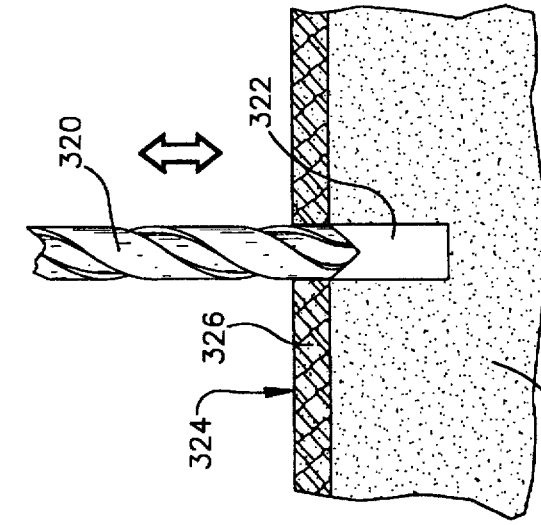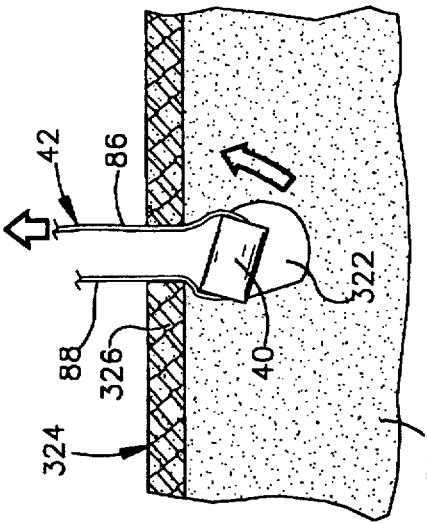

SUTURE ANCHOR INSERTER ASSEMBLY AND METHOD

BACKGROUND OF THE INVENTION

The present invention relates to an improved suture anchor inserter assembly and method of using the suture anchor inserter assembly to position a suture anchor in either soft or hard body tissue.

Surgeons utilize suture anchor inserter assemblies to position suture anchors in either soft body tissue or hard body tissue. Suture anchor inserter assemblies for positioning suture anchors in soft or hard body tissue are disclosed in U.S. Pat. Nos. 5,403,348 and 5,464,426. During the positioning of a suture anchor relative to body tissue, it is important that the suture anchor inserter assembly be constructed in such a manner as to facilitate accurate positioning of the suture anchor. Once the suture anchor has been accurately positioned relative to the body tissue, the suture anchor inserter assembly should be easily utilized to move the suture anchor into the body tissue.

SUMMARY OF THE INVENTION

The present invention relates to a new and improved suture anchor inserter assembly and method of using the suture anchor inserter assembly. The suture anchor inserter assembly includes a handle and a shaft which extends outward from the handle. The shaft may have a linear or non-linear configuration. A suture may extend through a passage in the shaft and the handle. The suture may be used to apply force to an anchor to hold the anchor in a chamber at an outer end of the shaft.

The shaft may advantageously be formed by relatively movable inner and outer members. A retainer assembly may hold the inner and outer members against relative movement until the anchor has been moved to a desired position relative to body tissue. Moving the anchor to a desired position relative to body tissue may be facilitated by deflecting body tissue with the shaft of the suture anchor inserter assembly.

Once the anchor has been moved to the desired position relative to the body tissue, the retainer assembly is manually actuated to release the inner and outer members for relative movement. During this relative movement, the anchor is inserted into either hard or soft body tissue.

In one embodiment of the invention, the outer member is movable relative to the inner member upon operation of the retainer assembly to a release condition. As the outer member is moved relative to the inner member, the outer member is advantageously moved into the handle. To facilitate gripping of the handle, the handle may advantageously have a triangular cross-sectional configuration.

The suture anchor inserter assembly may advantageously include a suture anchor insertion depth control assembly. This assembly is operable to limit the distance to which an anchor is inserted into body tissue.

BRIEF DESCRIPTION OF THE DRAWINGS

The foregoing and other features of the present invention will become more apparent upon a consideration of the following description taken in connection with the accompanying drawings, wherein:

FIG. 1 is a pictorial illustration of a suture anchor inserter assembly constructed in accordance with the present invention;

FIG. 2 is an enlarged fragmentary view, taken generally along the line 2—2 of FIG. 1, illustrating the manner in which a suture holds a suture anchor in a chamber formed in a shaft of the suture anchor inserter assembly;

FIG. 3 is an enlarged fragmentary sectional view, taken generally along the line 3—3 of FIG. 1, illustrating the manner in which the shaft extends outward from a handle of the suture anchor inserter assembly;

FIG. 4 is an enlarged view of a portion of FIG. 3 and illustrating a retainer assembly having an actuator member which retains a movable outer member which forms a portion of the shaft, against movement relative to a handle of the suture anchor inserter assembly;

FIG. 5 is a sectional view, taken generally along the line 5—5 of FIG. 4, further illustrating construction of the retainer assembly;

FIG. 6 is an enlarged view of a portion of FIG. 5;

FIG. 7 is a fragmentary sectional view, generally similar to FIG. 3 but on a reduced scale, illustrating the suture anchor inserter assembly when the actuator member has been moved from the engaged position of FIGS. 3–6 to a disengaged position;

FIG. 8 is a sectional view, taken generally along the line 8—8 of FIG. 7, further illustrating the retainer assembly with the actuator member in the disengaged position;

FIG. 9 is a fragmentary sectional view, generally similar to FIG. 7, illustrating the relationship between the outer member of the shaft and the handle when the outer member has been moved from the extended position of FIG. 7 to the retracted position of FIG. 9;

FIG. 10 is a sectional view, generally similar to FIG. 8, taken generally along the line 10—10 of FIG. 9;

FIG. 11 is a top plan view, taken generally along the line 11—11 of FIG. 5;

FIG. 12 is a side elevational view, taken generally along the line 12—12 of FIG. 11;

FIG. 13 is a side elevational view, taken generally along the line 13—13 of FIG. 11;

FIG. 18 is a schematic illustration depicting one way in which an opening may be formed in body tissue;

FIG. 19 is a schematic illustration depicting the manner in which a suture anchor is positioned relative to the opening of FIG. 18 by the suture anchor inserter assembly of FIG. 1;

FIG. 20 is a schematic illustration depicting the manner in which a suture anchor is moved into body tissue by the suture anchor inserter assembly of FIG. 1;

FIG. 21 is a schematic illustration depicting the manner in which the suture is tensioned to rotate the suture anchor relative to the body tissue;

FIG. 22 is a schematic illustration depicting the manner in which the suture is tensioned to press the suture anchor against body tissue;

FIG. 23 is an illustration of a second embodiment of the suture anchor;

3

Figure 24:
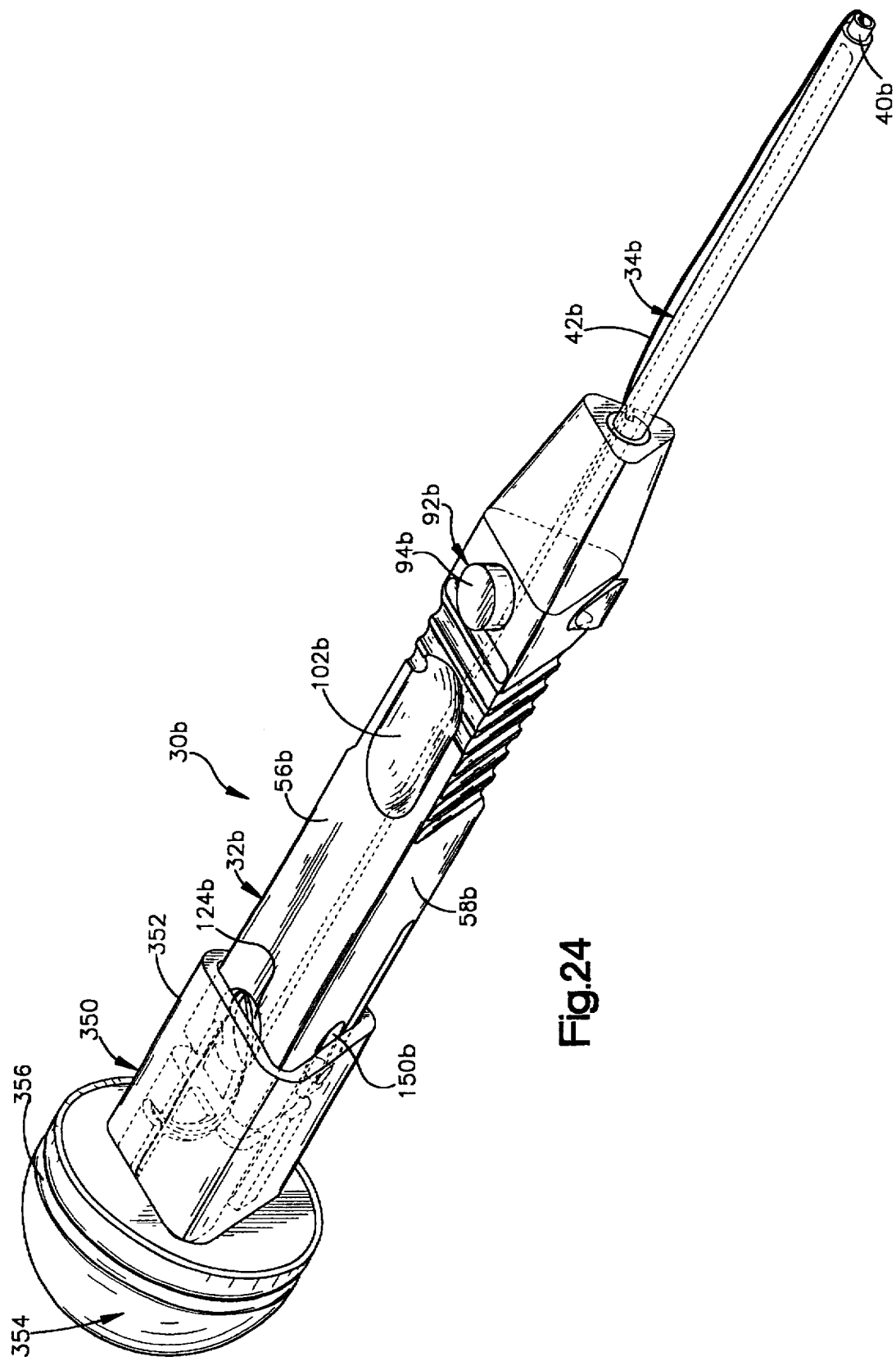
Figure 25:
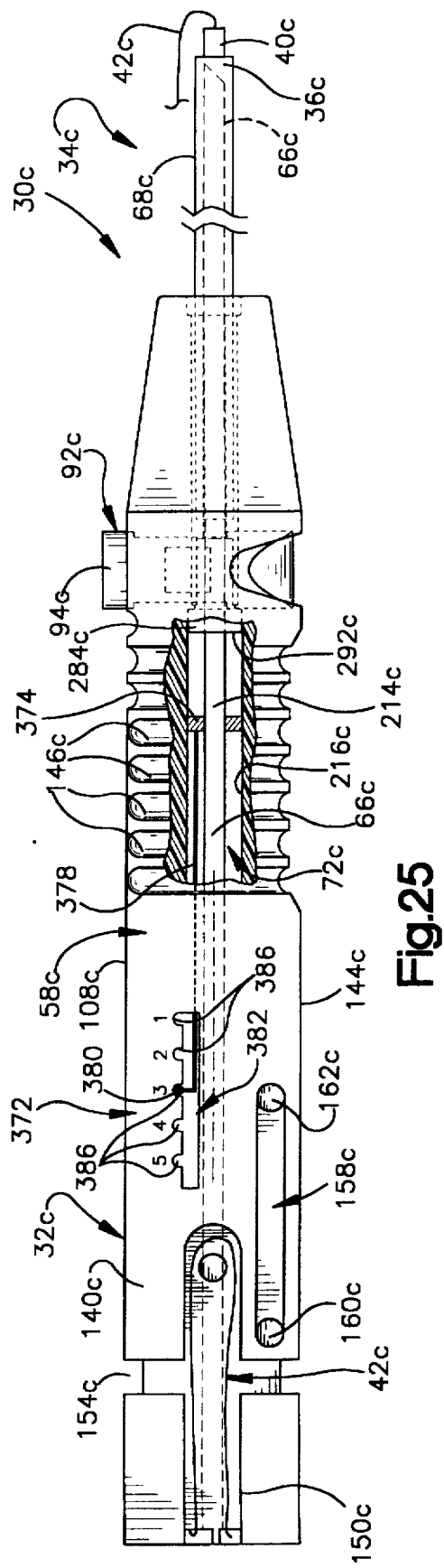
Figure 26:
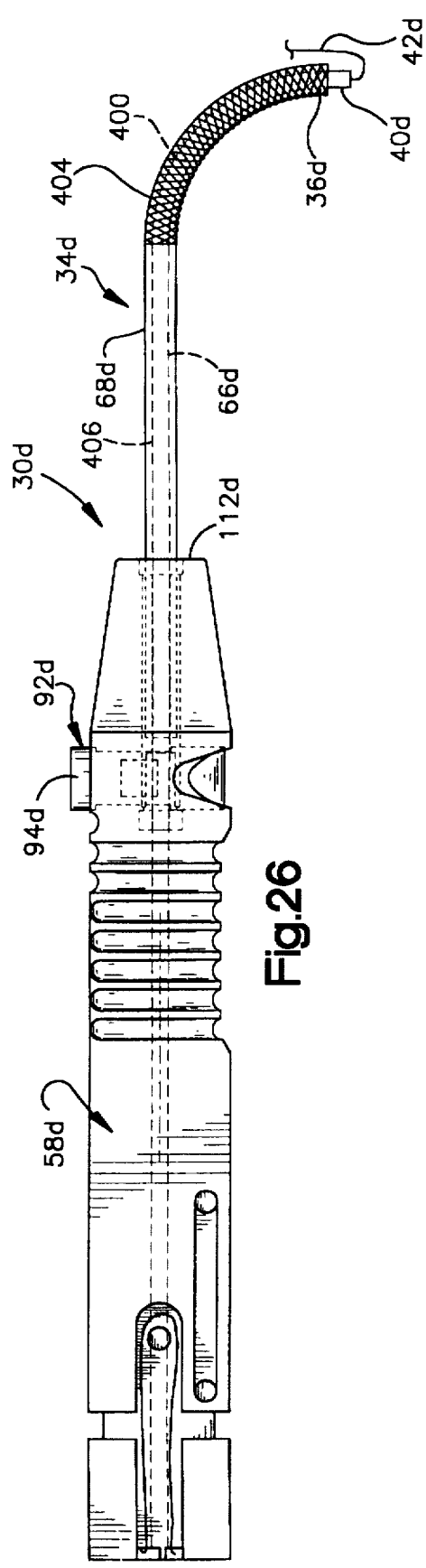

FIG. 24 is an illustration of a second embodiment of the suture anchor inserter assembly;

FIG. 25 is a side elevational view, similar to FIG. 12, of an embodiment of the suture anchor inserter assembly having an anchor insertion depth control assembly; and FIG. 26 is a side elevational view, similar to FIGS. 12 and 25, of an embodiment of the suture anchor inserter assembly having a non-linear shaft.

DESCRIPTION OF SPECIFIC PREFERRED EMBODIMENTS OF THE INVENTION

General Description

A suture anchor inserter assembly 30 constructed and used in accordance with the present invention is illustrated in FIG. 1. The suture anchor inserter assembly 30 includes a manually engageable handle 32 and a shaft 34 which extends axially outward from the handle. An outer or distal end portion 36 (FIG. 2) of the shaft 34 has a chamber 38 in which a suture anchor 40 is received. A suture 42 is affective to apply force against the anchor 40 to retain the anchor in the chamber 38.

The illustrated anchor 40 has a cylindrical tubular side wall 46. A trailing end portion 48 of the anchor 40 is received in the cylindrical chamber 38. It should be understood that the anchor 40 could have a construction different than the construction shown in FIG. 2. For example, the anchor 40 could have a polygonal cross sectional configuration if desired. Although it is preferred to form the anchor 40 of stainless steel, the anchor could be formed of biodegradable material or body tissue if desired.

A leading end portion 50 (FIG. 2) of the anchor 40 extends axially outward from the shaft 34. By having the anchor 40 extend outward from the shaft 34, accurate positioning of the anchor relative to body tissue is facilitated. The anchor 40 can be used to retain the suture 42 in either hard body tissue, such as bone, or soft body tissue, such as skin.

In accordance with one of the features of the invention, the handle 32 has a generally triangular cross-sectional configuration (FIGS. 1, 5, 14 and 15). The triangular cross-sectional configuration of the handle 32 facilitates comfortable gripping of the handle by a surgeon. In addition, the triangular cross-sectional configuration of the handle 32 facilitates accurate pointing of the shaft 34 and accurate positioning of the anchor 40 by the surgeon.

A first side 56 (FIGS. 1 and 11) of the handle 32 is engaged by the first finger on the right hand of the surgeon. A second side 58 (FIGS. 1 and 12) of the handle 32 is engaged by the second finger on the right hand of the surgeon. A third side 60 (FIGS. 1 and 13) is engaged by the thumb on the right hand of the surgeon. The thumb and first two fingers on the right hand of the surgeon cooperate to grip the handle in much the same manner as in which a pencil is gripped.

Figure 14:
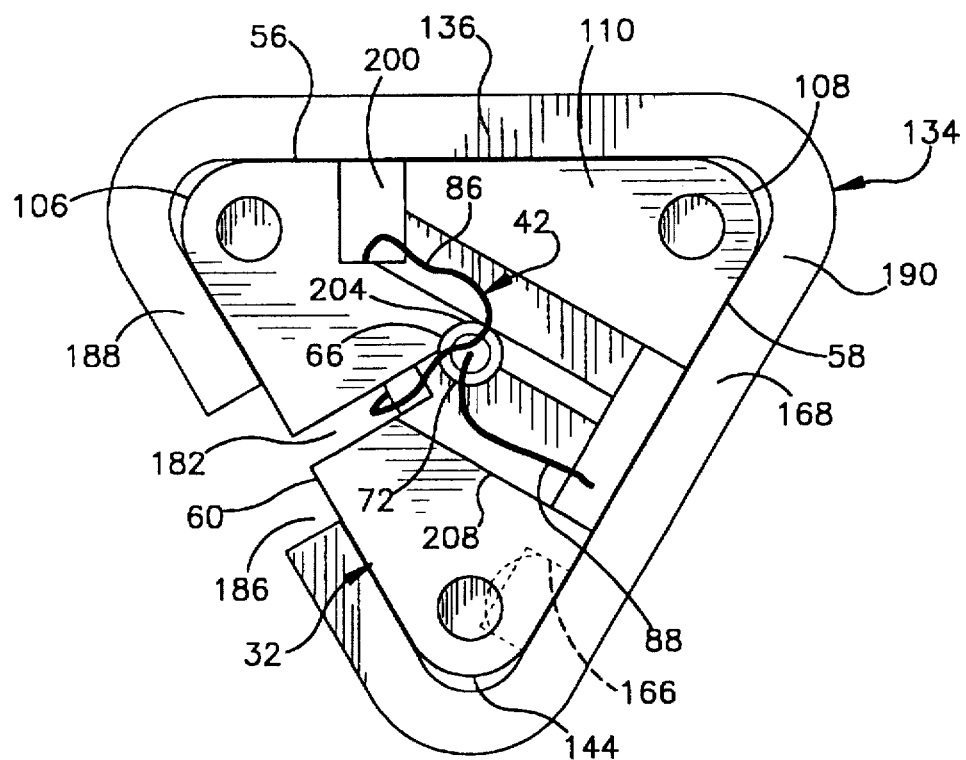
FIG. 14 is a proximal end view, taken generally along the line 14—14 of FIG. 1.
Figure 15:
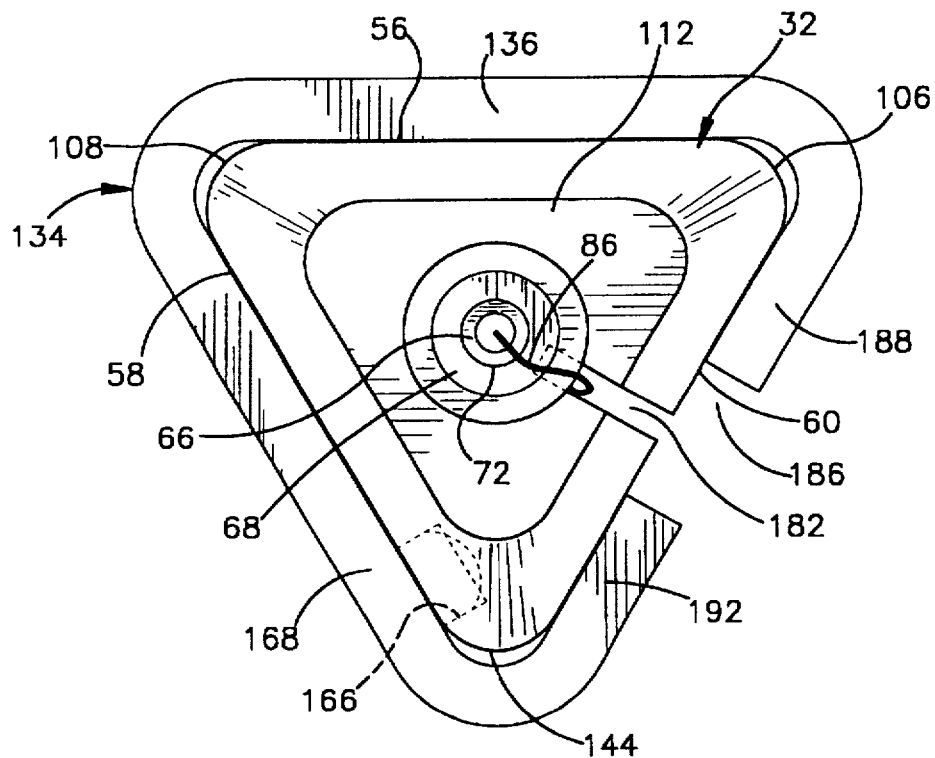
FIG. 15 is a distal end view, taken generally along the line 15—15 of FIG. 1.
Figure 16:
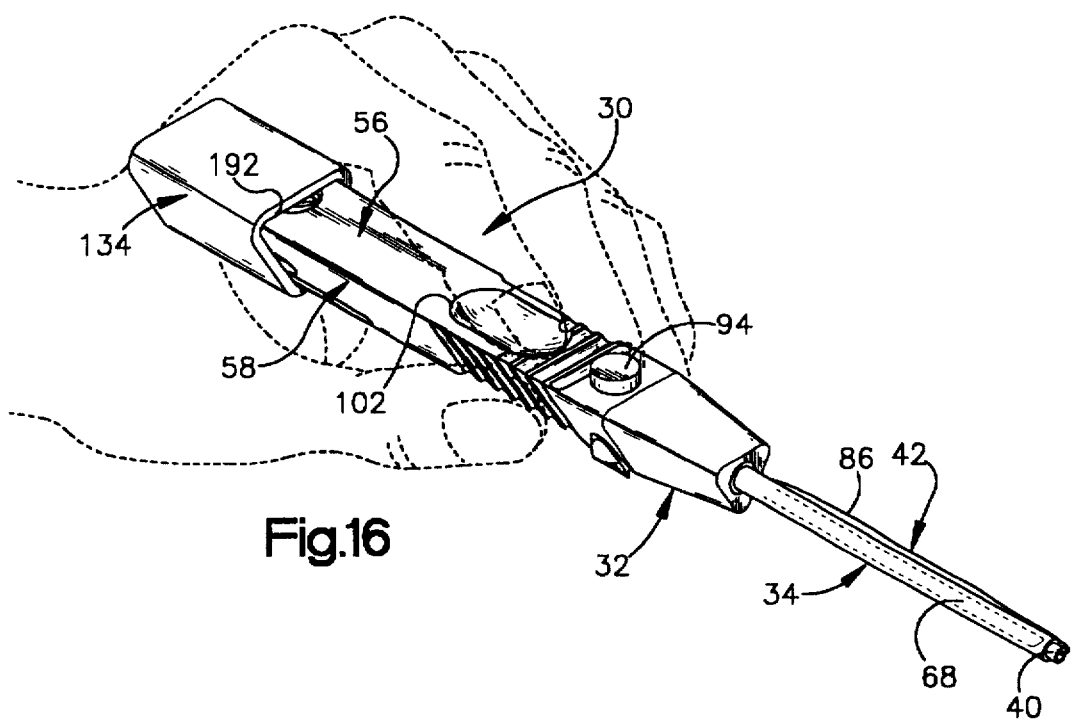
FIG. 16 is a pictorial illustration of the manner in which the handle of the suture anchor inserter assembly is manually gripped.
Figure 17:
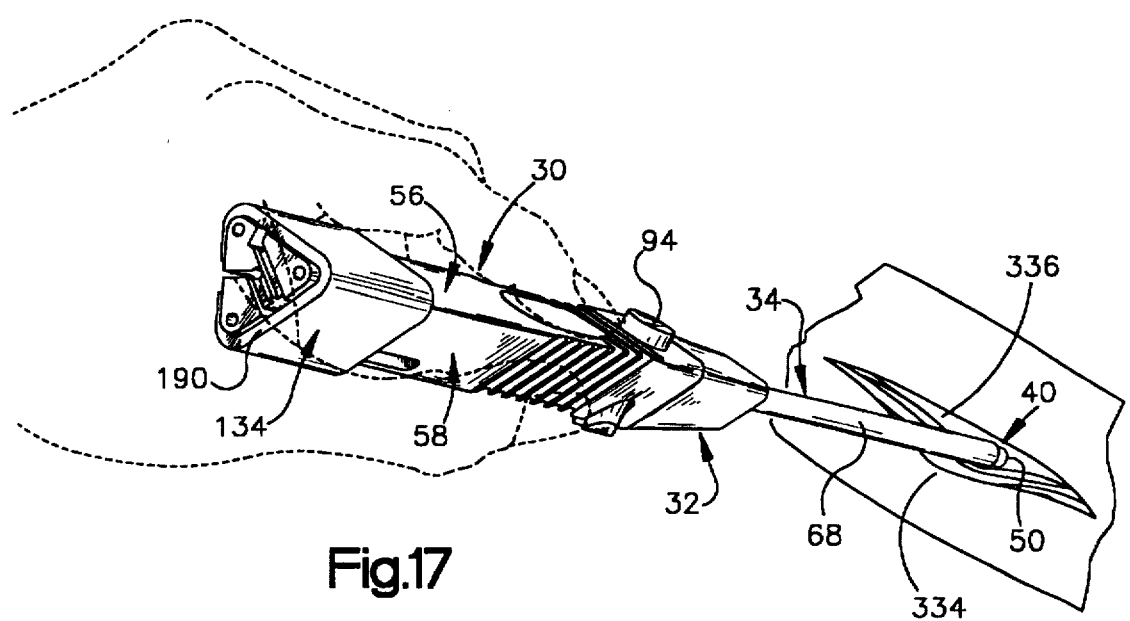
FIG. 17 is a pictorial illustration of the manner in which force is applied to the handle of the suture anchor inserter assembly to deflect body tissue with the shaft of the suture anchor inserter assembly.

If the surgeon is left handed or prefers to grip the suture anchor inserter assembly 30 with the left hand, the first finger on the left hand of the surgeon would engage the first side 56 of the handle 32 (FIGS. 11 and 16), the same as with a right handed grip. However, the second finger of the surgeon would engage the third side 60 (FIG. 13) of the handle 32. The left thumb of the surgeon would engage the second side 58 of the handle 32 (FIGS. 12, 16 and 17).

The triangular cross-sectional configuration of the handle 32 enables the suture anchor inserter assembly 30 to be easily gripped with either hand. In addition, the triangular cross-sectional configuration of the handle 32 results in offsetting forces being applied against the three sides 56, 58 and 60 of the handle. These offsetting forces are directed inward toward a longitudinal central axis of the handle. This results in the handle 32 being relatively stable in the hand of the surgeon when it is gripped by the surgeon.

In accordance with another of the features of the invention, the shaft 34 is formed by tubular inner and outer members 66 and 68 (FIGS. 2 and 3) which are relatively movable. The tubular inner member 66 has a cylindrical central passage 70 which is axially aligned with a cylindrical central passage 72 (FIG. 3) through the handle 32. The suture 42 extends through the passage 70 in the inner member 66 and through the passage 72 in the handle 32. The passages 70 and 72 through the shaft 34 and handle 32 have longitudinal central axes which are coincident with the longitudinal central axis of the handle 32. It should be understood that the inner and outer members 66 and 68 and passages 70 and 72 could have a configuration which is different than the illustrated cylindrical configuration.

The tubular inner member 66 has an inner end portion 76 (FIG. 1) which is fixedly connected with the handle 32. The connection between the inner end portion 76 of the tubular inner member 66 and the handle 32 holds the inner member 66 against movement relative to the handle 32. The tubular outer member 68 telescopically encloses a portion of the inner member 66. The outer member 68 cooperates with the inner member 66 to form the cylindrical chamber 38 (FIG. 2) in which the trailing end portion 48 of the anchor 40 is received.

The outer member 68 is axially movable along the inner member between an extended position (FIGS. 1, 2, 3 and 7) and a fully retracted position (FIG. 9). When the outer member 68 is in the extended position, an outer end portion 80 (FIG. 2) of the outer member 68 extends axially outward of the outer end portion 82 of the inner member 66. This results in the formation of the chamber 38 in the outer end portion 80 of the outer member 68. The inner end of the chamber 38 is formed by the outer end of the inner member 66.

The outer member 68 is axially movable along the stationary inner member 66 from the extended position of FIGS. 3 and 7 to the fully retracted position of FIG. 9. As the outer member 68 moves from the extended position (FIG. 7) to the fully retracted position (FIG. 9) the outer member 68 is telescopically moved into the handle 32. By sliding the outer member 68 into the handle 32, the overall length of the suture anchor inserter assembly 30 tends to be minimized. If desired, the outer member 68 could be fixedly connected to the handle 32 and the inner member 66 moved relative to the handle.

In accordance with another feature of the invention, the anchor 40 is held in the chamber 38 by the suture 42. The suture 42 has two sections or legs which extend from the anchor 40. Thus, an outer leg 86 (FIG. 1) of the suture 42 extends along the outside of the shaft 34 and into the handle 32. An inner leg 88 (FIG. 2) of the suture 42 extends through the anchor 40 and through the central passage 70 in the inner member 66. The inner leg 88 of the suture 42 also extends through the passage 72 (FIG. 3) in the handle 32.

Tension in the two legs 86 and 88 of the suture 42 enables the suture to apply force against the leading end portion 50 of the anchor 40 (FIG. 2). This force presses the trailing end portion 48 of the anchor against the outer end portion 82 of the inner member 66. The force applied against the anchor by the two legs 86 and 88 of the suture 42 retains the anchor 40 in the chamber 38 in the outer end portion 36 of the shaft 34. This enables the suture anchor inserter assembly 30 to be provided to a surgeon as a unit which is ready to be used.

In accordance with another feature of the invention, a retainer assembly 92 is manually operable between an engaged condition (FIGS. 3–6) retaining the inner and outer members 66 and 68 against relative movement and a disengaged condition (FIGS. 7–10) in which one of the inner and outer members is movable relative to the other. When the retainer assembly 92 is in the engaged condition (FIGS. 3–6) it retains the inner and outer members 66 and 68 against axial movement relative to each other. When the retainer assembly 92 is in the disengaged condition, the retainer assembly is ineffective to retain the inner and outer members 66 and 68 against axial movement relative to each other.

The retainer assembly 92 includes a manually operable actuator member 94 (FIGS. 1 and 3–10). The actuator member 94 is slidably mounted on the handle 32. The actuator member 94 is manually movable relative to the handle between the engaged position of FIGS. 3–6 and the disengaged position of FIGS. 7–10.

When the actuator member 94 is in the engaged position, the retainer assembly 92 holds the outer member 68 in the extended position shown in FIGS. 1 and 3. When the actuator member 94 is manually moved from the engaged position to the disengaged position of FIGS. 7–10, the retainer assembly 92 is operated to a disengaged condition. When the retainer assembly 92 is in the disengaged condition, the outer member 68 is released for axial movement from the extended position of FIG. 7 to the fully retracted position of FIG. 9. Thus, the outer member 68 is slidable along the inner member 66 into the handle 32 to the fully retracted position of FIG. 9 when the retainer assembly 92 is in the disengaged condition.

When a surgeon is using the suture anchor inserter assembly 30 to deflect body tissue and move an anchor 40 to a desired position relative to other body tissue, in the manner illustrated schematically in FIG. 17, the retainer assembly 92 is maintained in the engaged condition. At this time, the outer member 68 is held against axial movement relative to the handle 32. The suture 42 holds the trailing end portion 48 (FIG. 2) of the anchor 40 in the chamber 38. However, the leading end portion of the anchor 40 extends from the chamber 38 and the shaft 34 (FIG. 17) to facilitate visual alignment of the leading end portion 50 of the anchor 40 with the body tissue.

Once the anchor 40 has been moved to a desired position relative to the body tissue, the actuator member 94 is manually depressed by the first finger on the hand of the surgeon. This results in the retainer assembly 92 being operated from the engaged condition to the disengaged condition to release the outer member 68 for axial movement relative to the inner member 66 and handle 32. Axial movement of the shaft 34 relative to the body tissue and insertion of the anchor 40 into the body tissue then results in forces being applied by the body tissue against the outer member 68. These forces move the outer member 68 from the extended position of FIG. 7 toward the fully retracted position of FIG. 9 as the anchor 40 is inserted into the body tissue.

In accordance with another feature of the invention, the suture anchor inserter assembly 30 may be provided with a suture anchor insertion depth control assembly 372 (FIG. 25). The suture anchor insertion depth control assembly 372 limits the distance which an anchor is inserted into body tissue. This enables a surgeon to select a desired depth of anchor insertion and to set the suture anchor insertion depth control assembly 372 so that the suture anchor inserter assembly is operable to insert the anchor to the desired depth.

Although it is preferred to combine all of the various features of the suture anchor inserter assembly 30 into a single assembly, it is believed that the various features of the suture anchor inserter assembly could be used separately or in various combinations. For example, the triangular cross-sectional configuration of the handle 32 could be used without the axially movable outer member 68 and the retainer assembly 92. Similarly, the axially movable outer member 68 could be used with a handle having a different configuration than the illustrated triangular cross-sectional configuration of the handle 32 and without the retainer assembly 92. It is also contemplated that the retainer assembly 92 could be utilized with a shaft having an inner member which moves relative to an outer member.

Handle

The handle 32 advantageously has a triangular cross-sectional configuration (FIG. 5). The three sides 56, 58 and 60 of the handle 32 are all of the same size. The included angles between the three sides all equal to sixty degrees. Therefore, the handle 32 has an equilateral triangular cross sectional configuration.

The first side 56 (FIG. 11) of the handle 32 has a generally rectangular configuration. A longitudinal central axis of the first side 56 of the handle 32 extends parallel to the longitudinal central axis of the shaft 34. The longitudinal central axis of the first side 56 of the handle 32 extends perpendicular to and intersects a central axis of the actuator member 94.

The first side 56 of the handle 32 has a flat major side surface 100 (FIG. 11). A longitudinally extending recess 102 is formed in the major side surface 100. The recess 102 has a longitudinal central axis which is parallel to the longitudinal central axis of the major side surface 100 of the handle 32. The central axis of the recess 102 extends perpendicular to and intersects a central axis of the actuator member 94. The central axis of the recess 102 is parallel to and offset from the central axis of the shaft 34.

The first side 56 of the handle 32 has a pair of parallel corners 106 and 108. The corners 106 and 108 of the first side 56 of the handle 32 extend parallel to the central axis of the shaft 34. The corners 106 and 108 extend along the handle 32 between a proximal or inner end surface 110 and a distal or outer end surface 112 of the handle 32. The corners 106 and 108 taper inward toward each other on an axially tapering distal end portion 116 of the handle 32. The axially inward tapering distal end portion 116 of the handle has a configuration corresponding to the configuration of the frustrum of a tetrahedron.

A plurality of ribs 120 extend across the major side surface 100 of the handle 32. The ribs 120 extend perpendicular to the corners 106 and 108 of the handle 32 and to the longitudinal central axis of the shaft 34. The ribs 120 are partially disposed between the recess 102 and the actuator member 94. The ribs 120 are engageable by the first finger on the hand of a surgeon to minimize any tendency for the finger to slip.

A recess 124 (FIG. 11) is provided in the major side surface 100 to receive an arcuate needle 126 which is connected with an end of the outer leg 86 of the suture 42. The recess 124 includes a circular portion 128 in which the end of the needle 126 connected with the suture 42 is disposed. In addition, the recess 124 includes an arcuate portion 130 in which the body of the needle 126 is disposed.

A slide 134 (FIG. 1) covers the recess 124 to retain the needle 126 in the recess. The slide 134 has an equilateral triangular cross-sectional configuration and is axially movable along the handle 32. When the slide 134 is disposed in the closed position shown in FIG. 1, a rectangular side wall 136 on the slide blocks the recess 124 to retain the needle 126 and suture 42 in the recess. The slide 134 is movable axially along the handle 32 toward the shaft 34, that is, toward the right as viewed in FIG. 1, to an open position.

When the slide 134 is in the open position, the recess 124 is uncovered. When the recess 124 is uncovered, the end of the needle 126 connected with the suture 42 can be manually grasped at the relatively large circular section 128 (FIG. 11) of the recess 124. Once the needle has been removed from the recess 124, the slide may be returned to its closed position over the recess if desired.

The second side 58 (FIG. 12) of the handle 32 has a generally rectangular configuration. The second side 58 of the handle has a longitudinal central axis which is parallel to the longitudinal central axis of the shaft 34 and to the longitudinal central axis of the first side 56 (FIG. 11) of the handle. The longitudinal central axis of the second side 58 extends perpendicular to and is offset to one side of the central axis of the actuator member 94.

The second side 58 (FIG. 12) of the handle has a flat major side surface 140 which extends parallel to the central axis of the shaft 34. The major side surface 140 extends between the corner 108 and a corner 144. The corner 108 is formed between the major side surface 140 and the major side surface 100. The corners 108 and 144 extend parallel to each other and to the longitudinal central axis of the shaft 34.

A plurality of ribs 146 extend across the major side surface 140 (FIG. 12). The parallel ribs 156 extend perpendicular to the corners 108 and 144. The parallel ribs are engageable by the second finger on the right hand of a surgeon or by the thumb on the left hand of a surgeon to retard slippage between the hand of the surgeon and the handle 32. Some of the ribs 146 on the second side 58 of the handle 32 are aligned with the ribs 120 on the first side 56 (FIG. 11) of the handle 32.

An elongated recess 150 (FIG. 12) is formed in the major side surface 140. The recess 150 has a longitudinal central axis which extends parallel to the longitudinal central axis of the shaft 34. A cylindrical pin or peg 152 is disposed at the end of the recess 150 furthest from the proximal end surface 110 of the handle 32. The suture 42 extends around the pin 152. Although only a single turn of the suture 42 has been shown in FIG. 12 as extending around the pin 152, it is contemplated that a plurality of turns of the suture may extend around the pin. If desired, a second pin or peg could be provided in the recess 150 to facilitate coiling of the suture 42 in the recess.

Alternatively, the suture 42 could be wrapped around the handle in a recess 154. The recess 154 has a triangular cross-sectional configuration and extends along all three sides 56, 58 and 60 of the handle 32. If the excess length of suture is wrapped around the handle in the recess 154, the excess length of the suture would extend across the needle 126 (FIG. 11) and facilitate retaining the needle in the recess 124.

A second elongated recess 158 (FIG. 12) is provided in the second side 58 of the handle 32. The second recess 158 has a longitudinal central axis which extends parallel to the longitudinal central axis of the first recess 150 and to the longitudinal central axis of the shaft 34. A pair of relatively small circular recesses 160 and 162 are provided at opposite ends of the recess 158.

The recesses 160 and 162 releasably engage a detent 166 (FIG. 15) extending inward from a side wall 168 of the slide 134. When the slide 134 is in the closed position illustrated in FIG. 1, the detent 166 engages the recess 160 (FIG. 12) at the proximal end of the recess 158. When the slide 134 is moved along the handle 32 to the open position, the detent 166 engages the recess 162 at the opposite end of the recess 158.

The third side 60 (FIG. 13) of the handle 32 has a generally rectangular configuration. A central axis of the third side 60 of the handle extends parallel to a longitudinal central axis of the shaft 34. The longitudinal central axis of the third side 60 extends parallel to the longitudinal central axes of the first and second sides 56 and 58 (FIGS. 11 and 12). The longitudinal central axis of the third side 60 extends perpendicular to and is offset to one side of the central axis of the actuator member 94.

The third side 60 of the handle 32 has a flat major side surface 174 (FIG. 13). The side surface 174 has a generally rectangular configuration. The side surface 174 has a longitudinal central axis which extends parallel to the longitudinal central axis of the shaft 34. The central axis of the major side surface 174 of the third side 60 of the handle 32 extends parallel to the central axes of the major side surfaces 100 (FIG. 11) and 140 (FIG. 12) of the handle.

The major side surface 174 (FIG. 13) on the third side 60 of the handle 32 extends between parallel corners 106 and 144. The corner 106 is formed between the major side surface 174 (FIG. 13) and the major side surface 100 (FIG. 11). The corner 144 is formed between the major side surface 174 (FIG. 13) and the major side surface 140 of the handle 32.

A plurality of ribs 178 (FIG. 13) are formed in the third side 60 of the handle 32. The ribs 178 extend perpendicular to the corners 144 and 106. The ribs 178 are formed as continuations of the ribs 146 (FIG. 12) on the side 58 of the handle 32. The ribs 178 are engageable by the thumb on the right hand of a surgeon or the second finger on the left hand of a surgeon to retard slippage relative to the handle 32.

A longitudinally extending slot 182 is formed in the third major side 60 of the handle 32. The slot 182 extends parallel to the longitudinal central axis of the shaft 34 and to the longitudinal central axis of the handle 32. The slot 182 extends to the central passage 72 (FIGS. 3 and 18) which extends axially through the handle 32 and in which the tubular inner member 66 is disposed. An outer side surface of the tubular inner member 66 partially blocks a longitudinally extending inner portion of the slot 182. The slot 182 (FIG. 13) extends between the proximal end surface 110 and distal end surface 112 of the handle 32.

The slot 182 is aligned with an opening or slot 186 (FIGS. 14 and 15) in a side wall 188 of the slide 134 (FIGS. 5 and 8). The opening 186 extends between a proximal end surface 190 on the slide 134 (FIGS. 14 and 17) and a distal end surface 192 (FIGS. 15 and 16) on the slide. The outer leg 86 (FIGS. 1 and 2) of the suture 42 extends axially along the slot 182 (FIG. 13). The portion of the outer leg 86 of the suture 42 disposed in the slot 182 extends generally parallel to the longitudinal central axis of the shaft 34.

The proximal end portion of the handle 32 (FIG. 14) has an equilateral triangular configuration. Thus, the major sides 56, 58 and 60 are disposed in the triangular array and extend perpendicular to the proximal end surface 110 of the handle 32. The slide 134 has the same equilateral triangular cross-sectional configuration as the handle 32.

The proximal end surface 110 of the handle 32 has a plurality of recesses or channels which interconnect with recesses or channels in the sides 56 and 58 of the handle. A channel 200 (FIG. 14) extends from the recess 124 (FIG. 11) to accommodate the suture 42. The suture 42 extends from the slot 182 through channels formed in the proximal end surface 110 into the channel 200. The suture 42 extends across the channels formed in the proximal end surface 110 between the slot 182 and the channel 200. The portion of the suture 42 which extends through the channels in the proximal end surface 110 (FIG. 14) is engaged by a relatively sharp corner 204 which binds against the suture 42 to retard sliding movement and facilitate tensioning of the suture.

The outer leg 86 (FIGS. 1 and 2) of the suture 42 extends from the leading end portion 50 of the anchor 40 along the outside of the shaft 34. The outer leg 86 of the suture 42 extends longitudinally through the slot 182 between the proximal and distal end surfaces 112 and 110 (FIGS. 15 and 14) of the handle 32. The outer leg 86 of the suture then extends across the proximal end surface 110 (FIG. 14) of the handle 32 into the channel 200 leading to the recess 124.

The inner leg 88 (FIG. 2) of the suture 42 extends through the anchor 40. The inner leg 88 of the suture also extends through the passage 70 in the shaft 34 and the passage 72 (FIG. 3) in the handle 32 to the proximal end surface 110 (FIG. 14) of the handle. The inner leg 88 of the suture 42 then extends from the passage 72 in the handle through a channel 208 formed in the proximal end surface 110 to the recess 150 (FIG. 12) in the second side 58 of the handle. The leg 88 of the suture 42 extends around the pin 152 in the recess 150. Therefore, both legs 86 and 88 of the suture 42 extend across the proximal end surface 110 of the handle 32 and are received in recesses 124 or 150 formed in the handle. This enables tension to be maintained in the suture 42 so as to apply force against the leading end portion 50 (FIG. 2) of the anchor 40 to retain the anchor in the chamber 38.

The handle 32 and slide 134 are molded of suitable polymeric material. The handle 32 is molded around the inner end portion 76 (FIGS. 1 and 3) of the inner member 66 to fixedly secure the inner member to the handle. The slide 134 (FIG. 1) is molded separately from the handle. Of course, the slide 134 and handle 32 could be formed of a different material and in a different manner if desired.

Although it is preferred to form the handle 32 with three sides (56, 58 and 60) disposed in a triangular array, it should be understood that the handle could be formed with a different cross-sectional configuration if desired. For example, the handle 32 could have either a generally circular or oval cross-sectional configuration. Alternatively, the handle 32 could be formed with a polygonal cross-sectional configuration other than a triangular cross-sectional configuration. However, it is believed that the triangular cross-sectional configuration of the handle 32 will be preferred due to the high degree of comfort with which it can be manually gripped by a surgeon and the relatively high degree of stability which is obtained by applying offsetting forces to the sides (56, 58 and 60) of the handle.

In one specific embodiment of the invention, the handle 32 had an overall length of approximately 4¼ inches. In this specific embodiment of the invention, each of the sides 56, 58 and 60 of the handle had a width of approximately ⅝ of an inch. The shaft 34 extended outward from the handle for a distance of approximately 2¼ inches. It should be understood that the foregoing dimensions for the handle 32 and shaft 34 of the suture anchor inserter assembly 30 have been set forth herein for purposes of clarity of description and not for purposes of limitation of the invention. It is contemplated that the suture anchor inserter assembly 30 could be formed with a handle 32 and shaft 34 having many different sizes and/or configurations.

Shaft

The shaft 34 (FIG. 3) includes the cylindrical tubular inner member 66 and the cylindrical tubular outer member 68. The tubular cylindrical inner and outer members 66 and 68 are disposed in a coaxial telescopic relationship with each other. The cylindrical outer member 68 is movable axially relative to the inner member 66 and the handle 32. The inner end portion 76 of the inner member 66 is fixedly secured to the handle.

It is preferred to move the outer member 68 into the passage 72 in the handle 32 when the outer member is moved from the extended position of FIG. 7 toward the fully retracted position of FIG. 9. However, the outer member 68 could be shortened so as to move from the extended position to the fully retracted position without moving into the handle 32. It is believed that it will be preferred to have the outer member 68 extend into the handle 32 to facilitate retaining of the outer member by the retainer assembly 92.

A cylindrical passage 70 (FIG. 6) extends axially through the inner member 66. The cylindrical passage 70 in the inner member 66 is coaxial with the cylindrical passage 72 (FIGS. 3 and 4) in the handle 32. A cylindrical outer side surface 214 on the inner member 66 engages a cylindrical inner side surface 217 (FIG. 2) on the outer member 68.

The cylindrical outer side surface 214 (FIGS. 3 and 4) on the inner member 66 is spaced from and is coaxial with a cylindrical inner side surface 217 of a large diameter portion 218 of the passage 72 through the handle 32 (FIGS. 3 and 4). The inner end portion 76 of the inner member 66 has the same diameter as a small diameter portion 220 (FIG. 3) of the passage 72 in which the inner end portion 76 of the inner member is disposed. The polymeric material of the handle 32 is bonded to outer side surfaces 214 of the inner end portion 76 of the inner member 66 to fixedly connect the inner member 66 with the handle. Of course, a mechanical interlock could be used to fixedly interconnect the inner member 66 and the handle 32.

The inner member 66 has a pointed outer end portion 82 (FIG. 2). The outer portion 82 is cut at an angle of approximately 45° to the central axis of the inner member 66. The pointed or tapered end portion 82 of the inner member 66 applies a concentrated force against the trailing end portion 48 of the anchor 40 to push the anchor into body tissue. The force which is applied against the anchor 40 by the inner member 66 is transmitted from the handle 32 through the inner member to the anchor.

The tubular cylindrical outer member 68 is coaxial with the inner member 66 and has a cylindrical inner side surface 216 (FIG. 2) which slides on the cylindrical outer side surface 214 of the inner member 66. The outer member 68 is axially slidable along the cylindrical outer side surface 214 on the inner member 66 between the extended position of FIG. 7 and the fully retracted position of FIG. 9. When the outer member 68 is in the extended position of FIG. 7, it extends beyond the outer end portion of the inner member 66 and encloses the trailing end portion of the anchor 40. When the outer member 68 is in the fully retracted position of FIG. 9, the outer member is partially telescoped into the handle 32 and the inner member 66 extends beyond the outer end portion of the outer member.

In the illustrated body of the invention, the inner and outer members 66 and 68 have a cylindrical tubular configuration. However, it is contemplated that the inner and outer members 66 and 68 could have a different configuration if desired. For example, the inner and outer members 66 and 68 could both have a triangular cross-sectional configuration as viewed on a plane extending perpendicular to their coincident longitudinal central axes. Although it is preferred to fixedly secure the inner member 66 with the handle 32 and telescopically move the outer member 68 relative to the inner member, the handle 32 could be connected with the inner and outer members in such a manner that the inner member 66 is movable relative to the handle and outer member 68. Thus, the outer member 68 could be fixedly connected with the handle 32 and the inner member moved axially relative to the handle to move an anchor 40 into body tissue.

In the illustrated embodiment of the invention, the anchor 40 has a tubular cylindrical configuration. However, it is contemplated that the anchor could have a different configuration if desired. For example, the anchor 40 could have a triangular cross-sectional configuration as viewed in a plane extending perpendicular to a central axis of the anchor. An anchor having such a construction is disclosed in U.S. patent application Ser. No. 08/291,970 filed Aug. 17, 1994 by Peter M. Bonutti and entitled "Method and Apparatus for Anchoring a Suture". If an anchor having the triangular cross-sectional configuration of the anchor disclosed in the aforementioned U.S. patent application Ser. No. 08/291,970 was used in association with the suture anchor inserter assembly 30, it is believed that it may be preferred to utilize inner and outer members 66 and 68 having triangular cross-sectional configurations which correspond to the triangular cross-sectional configuration of the anchor in order to facilitate retaining the anchor in the chamber 38 at the end of the shaft 34. However, it is contemplated that the inner and outer members 66 and 68 of the shaft 34 could have a cross-sectional configuration which is different from the cross-sectional configuration of anchor which is to be inserted in the body tissue by the suture anchor inserter assembly 30.

In the illustrated embodiment of the suture anchor inserter assembly 30, the handle 32 is used with the shaft 34. However, it is contemplated that a different shaft could be used with the handle 32 or a different handle could be used with the shaft 34. Thus, the handle 32 could be used with a shaft which is formed as one-piece. Alternatively, the shaft 34 could be used with a handle having a configuration which is different than the configuration of the handle 32.

Retainer Assembly

The retainer assembly 92 is manually operable from an engaged condition to a disengaged condition to release the outer member 68 for axial movement relative to the inner member 66. When the retainer assembly 92 is in the engaged condition, the inner and outer members 66 and 68 are held against axial movement relative to the handle 32 and to each other.

Upon operation of the retainer assembly 92 to the disengaged condition, the outer member 68 is released for axial movement relative to the handle 32 and the inner member 66. Thus, upon operation of the retainer assembly 92 to the disengaged condition, the outer member 68 can be moved from the extended position of FIG. 7 toward the fully retracted position of FIG. 9. As this occurs, the extent of the outer member 68 enclosed by the handle 32 increases.

The retainer assembly 92 includes the generally cylindrical actuator member 94 and a generally cylindrical retainer sleeve 230 (FIGS. 3 and 4). The retainer sleeve 230 is fixedly connected with the outer member 68. The retainer sleeve 230 is disposed in a coaxial relationship with the outer member 230.

When the actuator member 94 is in the engaged condition of FIGS. 4, 5 and 6, the actuator member 94 engages stop surfaces connected with the retainer sleeve 230 to block axial movement of the retainer sleeve and outer member 68 relative to the handle 32. When the actuator member 94 has been moved to the disengaged position of FIGS. 7–10, the retainer sleeve 230 and the outer member 68 are axially movable relative to the actuator member 92 and handle 32. Thus, when the actuator member 94 is in the disengaged position shown in FIGS. 7–10, the retainer sleeve 230 is axially movable relative to the handle 32 from the position shown in FIG. 7 to the position shown in FIG. 9.

The actuator member 94 has a generally cylindrical configuration and includes a manually engageable head end portion 236. The actuator member 94 is slidably supported by a cylindrical guide surface 238 molded in the handle 32. A pair of parallel leg portions 240 and 242 extend downward (as viewed in FIGS. 5 and 6) from the head end portion 236 and engage the guide surface 238. The leg portions 240 and 242 are separated by a slot 244.

The slot 244 extends diametrically through the actuator member 94 and includes a relatively small rectangular retaining section 250 and a relatively large rectangular release section 252 (FIG. 6). The retaining section 250 and release section 252 have central axes which are coincident with a central axis 254 of the actuator member 94 and slot 244. The central axis 254 of the actuator member 94 extends perpendicular to and intersects a central axis of the inner member 66 of the shaft 34.

The rectangular retaining section 250 of the slot 244 in the actuator member 94 cooperates with the retainer sleeve 230 to hold the retainer sleeve against axial and rotational movement. Thus, the rectangular retainer section 250 (FIG. 6) has a pair of flat parallel side surfaces 258 and 260. The flat side surfaces 258 and 260 on the actuator member 94 engage the retainer sleeve 230 to hold the retainer sleeve and outer member 68 against axial and rotational movement relative to the inner member 66.

The relatively large rectangular release section 252 of the slot 244 in the actuator member 94 has a pair of flat parallel side surface 264 and 266. The flat parallel side surfaces 264 and 266 of the release section 252 are spaced equal distances from the central axis 254 of the actuator member 94. The flat parallel side surfaces 264 and 266 of the release section 252 extend parallel to the flat side surfaces 258 and 260 of the retaining section 250 of the slot 244 in the actuator member 94. However, the flat side surfaces 264 and 266 on the release section 252 of the actuator member 94 are spaced further apart than are the side surfaces 258 and 260 on the retaining section 250.

A pair of rectangular notches 270 and 272 are formed in the outside of the leg portions 240 and 242. The notch 272 cooperates with the slot 182 and the handle 32 to grip a portion of the outer leg 86 of the suture 42. The suture 42 is gripped between a corner portion 276 of the notch 272 and the handle 32 when the actuator member 94 is in the engaged position of FIG. 6. The gripped portion of the suture 42 is securely held against movement relative to the handle 32. This facilitates the maintaining of tension in the suture 42 to apply force holding the anchor 40 in the chamber 38 of the suture anchor inserter assembly 30.

When the actuator member 94 is moved to the disengaged position of FIG. 8, the suture 42 is released by the actuator member. As the actuator member 94 is moved from the engaged position of FIG. 6 to the disengaged position of FIG. 8, the notch 272 opens to the slot 182. As this occurs, the corner portion 276 (FIG. 6) of the notch 272 moves away from the suture 42 (FIG. 8).

Only the notch 272 engages the suture 42. The opposite notch 270 is provided in order to enable the actuator member 94 to be installed in the handle 32 in the illustrated orientation or in an orientation offset 180° from the illustrated orientation.

The actuator member 94 cooperates with the retainer sleeve 230 to hold the outer member 68 against axial rotational movement relative to the handle 32 when the actuator member is in the engaged position of FIGS. 3 and 4. The retainer sleeve 230 includes a generally cylindrical body portion 282 which is disposed in a coaxial relationship with the inner and outer members 66 and 68. An annular inner bearing ring 284 is connected to an axially inner end of the body portion 282 of the retainer sleeve 230. Similarly, an annular outer bearing ring 286 (FIG. 3) is connected to the outer end of the body portion 282 of the retainer sleeve 230.

The inner and outer bearing rings 284 and 286 engage the cylindrical inner side surface 217 of the large diameter portion 218 of the passage 72. During movement of the outer member 268 from the extended position of FIG. 7 to the fully retracted position of FIG. 9, the coaxial bearing rings 284 and 286 slide along the inner side surface 217 of the passage 72 to guide movement of the retainer sleeve 230 relative to the handle 32.

The outer member 68 extends axially into and is coaxial with the cylindrical body portion 282 (FIG. 4) of the retainer sleeve 230. An inner end 290 of the outer member 68 is disposed adjacent to the actuator member 94 when the outer member is in the extended position of FIG. 3. The body portion 282 of the retainer sleeve 230 is fixedly bonded to the inner end portion of the outer member 68.

When the retainer sleeve 230 is moved axially relative to the passage 72 in the handle 32, the outer member 68 moves axially with the retainer sleeve relative to the passage. Similarly, when the retainer sleeve 230 is held against axial movement relative to the passage 72 in the handle 32 by the actuator member 94, the outer member 68 is held against axial movement relative to the passage 72.

An annular stop surface 291 (FIG. 4) on the bearing ring 284 is engageable with the actuator member 94 to limit outward movement, that is, toward the right as viewed in FIG. 4, of the outer member 68. An annular stop surface 292 on the bearing ring 284 is engageable with an annular stop or end surface 293 (FIG. 3). The stop or end surface 293 is disposed between the large diameter portion 218 and small diameter portion 220 of the passage 72. Engagement of the stop surface 292 with the stop surface 293 limits inward movement, that is movement toward the left as viewed in FIG. 3, of the outer member 68. Alternatively, if desired, the spacing between the bearing rings 284 and 286 could be decreased or the axial extent of the large diameter portion 218 of the passage 72 increased to enable an annular stop surface 294 on the bearing ring 286 to engage the actuator member 94 to limit inward movement of the outer member 68.

The generally cylindrical body portion 282 of the retainer sleeve 230 has a pair of parallel rectangular retainer flats 296 and 298 (FIG. 6) which are disposed on opposite sides of the retainer sleeve 230. The retainer flat 296 extends axially along the body portion 282 (FIG. 4) of the retainer sleeve 230 for a distance which is equal to the width of the leg portions 240 and 242 (FIG. 6) of the actuator member 94. The retainer flat 298 has the same rectangular configuration and size as the retainer flat 296.

The retainer flat 296 has a stop surface or shoulder 302 (FIG. 4) which is engageable by the leg portion 240 (FIG. 6) of the actuator member 94. The shoulder 302 extends perpendicular to and is offset to one side of the central axis of the shaft 34. A shoulder or stop surface, similar to and parallel to the shoulder 302, is formed on the retainer flat 298 to engage the leg portion 242 of the actuator member 94. The parallel stop surfaces 291 and 302 (FIG. 4) engage the actuator member 94 to block axial movement of the retainer sleeve 230 and outer member 68 when the actuator member 94 is in the engaged position. The retainer flats 296 and 298 cooperate with the leg portions 240 and 242 (FIG. 6) to hold the retainer sleeve 230 and outer member 68 against rotation about their coincident central axes.

Upon movement of the actuator member 94 from the engaged position of FIGS. 5 and 6 to the disengaged position of FIGS. 7–10, the release section 252 of the slot 244 in the actuator member 94 moves into alignment with the retainer flats 296 and 298 (FIG. 8). The side surfaces 264 and 266 (FIG. 6) of the release section 252 of the slot 244 are spaced further apart than are the side surfaces 258 and 260 of the retainer section 250 of the slot 244. Therefore, the retainer surfaces 296 and 298 are spaced from the leg portions 240 and 242 of the actuator member 94 (FIG. 8) when the actuator member is in the disengaged position.

The cylindrical body portion 282 of the retainer sleeve 230 has a pair of parallel rectangular guide flats 310 and 312 (FIG. 8) which extend parallel to the retainer flats 296 and 298 (FIG. 6). The guide flat 310 (FIGS. 3 and 4) extends between the shoulder 302 (FIG. 4) and the bearing ring 286. Similarly, the guide flat 312 extends between the shoulder at the axially outer end of retainer flat 298 (FIG. 6) and the bearing ring 286. The guide flat 312 has the same rectangular configuration and size as the guide flat 310.

The guide flats 310 and 312 are spaced apart by a distance which is the same as the spacing between the side surfaces 264 and 266 (FIG. 6) of the release section 252 of the slot 244 in the actuator member 94. When the actuator member 94 has been depressed from the engaged position of FIG. 6 to the disengaged position of FIG. 8, the guide flats 310 and 312 are aligned with the opposite side surfaces 264 and 266 of the release section 252 of the slot 254. This enables the outer member 68 to be moved from the extended position of FIG. 7 toward the fully retracted position of FIG. 9.

As the outer member 68 moves from the extended position toward the fully retracted position, the guide flats 310 and 312 (FIG. 10) slide along the side surfaces 264 and 266 of the release section 252 of the actuator member 94. When the outer member 68 reaches the fully retracted position of FIG. 9, the guide ring 286 is adjacent to the leg portions 240 and 242 of the actuator member 94. The guide flats 310 and 312 cooperate with the leg portions 240 and 242 to hold the retainer sleeve 230 and outer member 68 against rotation about their coincidental central axes.

A retainer assembly having a different construction than the retainer assembly 92 could be utilized to hold the outer member 68 against axial movement relative to the inner member 66. For example, a pivotal lever could have a nose portion which engages a suitable detent in the outer member 68. Upon manual actuation of the retainer assembly to pivot the lever, the nose portion of the lever would move out of engagement with the detent in the outer member 68 to release the outer member for movement relative to the inner member 66.

In embodiments of the invention in which the inner member 66 is movable relative to the outer member 68, the retainer assembly 92 could be constructed in such a manner as to hold the inner member against axial movement relative to the outer member. Manual force could then be applied to the retainer assembly to move the inner member 66 relative to the outer member 68. For example, the suture anchor inserter assembly 30 could be constructed so that a projection from the inner member 66 moves along the handle 32 to move the inner member relative to the outer member 68 which is fixedly connected with the handle.

Use of Inserter Assembly

When the suture anchor inserter assembly 30 is to be used to insert an anchor 40 into body tissue, a surgeon grips the suture anchor inserter assembly 30 in a manner illustrated in FIGS. 16 and 17. At this time, the retainer assembly 92 is in the engaged condition of FIGS. 3–6. In FIGS. 16 and 17, the suture anchor inserter assembly 30 has been shown as being gripped by the left hand of a surgeon. Of course, the suture anchor inserter assembly 30 could be gripped in the right hand of a surgeon if desired.

When the suture anchor inserter assembly 30 is gripped by the left hand of a surgeon, as shown in FIGS. 16 and 17, the first finger is effective to apply force against the recess 102 (FIG. 11) in the first side 56 of the suture anchor inserter assembly. This force is directed inward toward the central axis of the handle 32. The thumb of the surgeon is effective to apply force against the ribs 146 along the side 58 (FIGS. 12, 16 and 17) of the handle 32. This force is directed inward toward the central axis of the handle 32. The second finger on the hand of the surgeon is effective to apply force against the ribs 178 (FIG. 13) on the third side 60 of the handle 32. This force is also directed inward toward the central axis of the handle.

As was previously explained, the handle 32 can be easily gripped by either the right or the left hand of a surgeon. Regardless of which hand is used, the triangular cross-sectional configuration of the handle 32 results in offsetting the forces being applied by the thumb and fingers of the surgeon against the sides of the handle 32. This results in the handle 32 being relatively stable when it is gripped between the thumb and first two fingers on the hand of the surgeon.

When the surgeon first grips the suture anchor inserter assembly 30, tension in the suture 42 holds the anchor 40 in the recess 38. The needle 126 (FIG. 11) at the end of the outer leg 86 of the suture is securely held in the recess 124. In addition, a portion of the outer leg 86 which extends through the slot 182 (FIG. 13), is gripped between the corner portion 276 (FIG. 6) of the notch 272 in the actuator member 94 and handle 32. The coiled end portion inner leg 88 (FIG. 12) is securely retained around the pin 152 in the recess 150. At this time, the slide 134 is in the closed position (FIG. 1) covering the recesses 124 and 150.

When the suture anchor 40 is to be inserted into relatively hard body tissue, for example bone, a drill 320 (FIG. 18) is utilized to drill a hole or opening 322 in the bone 324. The hole 322 is drilled through the hard compact outer layer 326 of bone and extends into the spongy cancellous inner bone 328. After the opening 322 has been formed by the drill 320, the drill is removed from the opening.

The leading end portion 50 of the anchor 40 is then moved into the opening 322. At this time, the retainer assembly 92 (FIG. 1) holds the inner and outer members 66 and 68 against movement relative to each other. The anchor 40 is held in the chamber 38 by force applied against the leading end portion 50 of the anchor by tension in the two legs 86 and 88 of the suture 42.

As the leading end portion 50 (FIG. 19) of the anchor 40 enters the opening 322, the leading end of the outer member 68 moves toward the layer 326 of hard compact bone. When the leading end of the outer member 68 engages the layer 326 of hard compact bone 324, further movement of the anchor 40 into the opening 322 is blocked. The surgeon then depresses the actuator member 94 with his first finger. This releases the outer member 68 for axial movement relative to the inner member 66. In addition, the portion of the outer leg 86 of the suture 42 gripped in the notch 272 (FIG. 6) in the actuator member 94 is released.

After the actuator member 94 has been manually moved to the disengaged position (FIG. 7), the outer member 68 is free to move axially relative to the inner member 66. Force is then applied against the handle 32 by the hand of the surgeon (FIGS. 16 and 17). This force is transmitted through the inner member 66 to the trailing end portion 48 (FIG. 2) of the anchor 40. The anchor 40 is moved into the opening 322 in the bone 324 in the manner indicated schematically in FIG. 20. As this occurs, a leading end portion of the inner member 66 is extended axially outward of the leading end portion of the outer member 68. Thus, the leading end portion of the inner member 66 enters the opening 322 in the body tissue while the outer member 68 remains outside of the opening in the body tissue (FIG. 20).

As the inner member 66 moves into the opening 322 (FIG. 20), the hard outer layer 326 of the bone 324 applies force to the leading end of the outer member 68 and moves the outer member from the extended position of FIG. 7 toward the fully retracted position of FIG. 9. The extent of movement of the outer member 68 relative to the inner member 66 will vary as a function of the depth to which the anchor 40 is inserted into the opening 322. Of course, the greater the depth which the anchor 40 is inserted into the opening 322, the greater is the distance which the outer member 68 is telescopically moved into the handle 32 (FIGS. 7 and 9).

As the anchor 40 is inserted into the opening 322 (FIGS. 19 and 20), the pointed end portion 82 (FIGS. 2 and 20) of the inner member 66 applies a concentrated force against the trailing end portion 48 of the anchor 40. This force pivots the anchor relative to the central axis of the shaft 34 (FIG. 20). As this occurs, the leg 86 of the suture 42 is tensioned to apply force against the leading end portion 50 of the anchor to further promote a counterclockwise (as viewed in FIG. 20) rotational movement of the anchor 40.

The shaft 34 of the suture anchor inserter assembly 30 is then disengaged from the bone 324 and the anchor 40. The leg 86 of the suture 42 is then tensioned to continue the counterclockwise pivoting movement (as viewed in FIG. 21) of the anchor 40. The legs 86 and 88 of the suture 42 are then tensioned (FIG. 22) to pull the anchor 40 against the hard layer 326 of compact bone. Engagement of the anchor 40 with the hard compact outer layer 326 of bone results in the suture 42 being securely held in place. The manner in which the anchor 40 is pivoted relative to the bone 324 is similar to that described in U.S. Pat. No. 5,403,348 issued Apr. 4, 1995 and entitled "Suture Anchor".

In the illustrated embodiment of the invention, the tubular cylindrical anchor 40 has a length which is between 2 mm and 4 mm. The suture anchor has a cylindrical central passage with a diameter of about one-half millimeter. The diameter of the suture anchor may range from 1 mm to 3 mm. A suture anchor having this general construction had an average pull-out load of 29.5 lbs. with a #2 suture. This results in the suture anchor having a relatively high pull-out strength so that a relatively small anchor can carry a relatively large load.

In FIGS. 18–22, insertion of the suture anchor 40 into hard body tissue has been schematically illustrated. However, it is contemplated that the suture anchor 40 and suture anchor inserter assembly 30 will be utilized in association with relatively soft body tissue. The suture anchor inserter assembly 30 may be used to position the suture anchor 40 in soft tissue in a manner similar to that disclosed in U.S. Pat. No. 5,464,426 issued Nov. 7, 1995 and entitled "Method of Closing Discontinuity in Tissue".

During insertion of the suture anchor 40 into the body tissue, it is contemplated that it may be desirable to move soft body tissue aside and align the anchor with body tissue which is uncovered by the sideward movement of the soft body tissue. The manner in which the suture anchor inserter assembly 30 may be used to deflect soft body tissue 334 to one side is illustrated schematically in FIG. 17.

When soft body tissue 334 is to be moved to one side, the hand of the surgeon applies a sideward force to the handle 32 of the suture anchor inserter assembly 30. This force acts in a direction transverse to the central axis of the shaft 34 and handle 332. The force is transmitted from the handle 32 to the shaft 34. The force presses the outer side surface of the outer member 68 against the body tissue 334. The sideward force applied against the body tissue 334 by the shaft 34 of the suture anchor inserter assembly 30 displaces the body tissue sideward relative to underlying body tissue 336.

Once the underlying body tissue 336 (FIG. 17) has been exposed by forcing the overlying outer body tissue 334 to one side with the shaft 34 of the suture anchor inserter assembly 30, the leading end portion 50 of the anchor 40 can be visually aligned with the underlying body tissue 336 by the surgeon. Aligning the anchor 40 with the underlying body tissue 336 is facilitated by the fact that the leading end portion 50 (FIG. 2) of the anchor is exposed and projects forward of the outer end portion 36 of the shaft 34. At this time, tension in the suture 42 holds the anchor 40 in the chamber 38 in the outer end portion 36 of the shaft 34.

The anchor 40 can then be inserted into the exposed underlying body tissue 336 (FIG. 17). To insert the anchor 40 into the body tissue 336, the leading end of the anchor is pressed firmly against the body tissue. The actuator member 94 is then manually moved to the disengaged position. This releases the outer member 68 for sliding movement along the inner member 66 into the handle 32.

If desired, the suture 42 may be used to tie the body tissue 324 back in the position to which it was moved by the force applied against the body tissue by the shaft 34. For example, a tendon may be deflected to one side by the shaft 34 and the anchor 40 inserted into a bone. The suture 42 can then be used to secure the tendon in position on the bone. Of course, the underlying body tissue 336 could be soft body tissue.

If the body tissue 334 which is forced aside with the shaft 34 of the suture anchor inserter assembly 30 overlies relatively soft body tissue 336, the leading end portion 50 of the anchor 40 may be pressed against the relatively soft body tissue to perforate an imperforated surface of the soft body tissue. After this has been done, the actuator member 94 is operated to disengage the retainer assembly 92. Once this occurs, force manually applied against the handle 32 is transmitted through the inner member 66 and the anchor 40 to force the anchor further into the relatively soft body tissue 336. Alternatively, if the body tissue exposed by forcing the body tissue 334 aside is relative hard body tissue, it may be desirable to drill an opening, similar to the opening 322 of FIG. 18, in the exposed hard body tissue. Once this has been done, the anchor 40 would be inserted into the opening.

Anchor—Second Embodiment

The anchor 40 has a flat annular leading end surface. Since the anchor 40 is relatively small and the side wall 46 of the anchor is relatively thin, the flat leading end surface of the anchor 40 may be able to satisfactorily form an opening in imperforate body tissue. In the embodiment of the anchor illustrated in FIG. 23, the anchor has a relatively sharp leading end portion to facilitate the perforating of body tissue with the anchor. Since the embodiment of the invention illustrated in FIG. 23 is generally similar to the embodiment of the invention illustrated in FIGS. 1–22, similar numerals will be utilized to designate similar components, the suffix letter "a" being added to the numerals of FIG. 23 to avoid confusion.

A suture anchor 40a (FIG. 23) has a tubular cylindrical side wall 46a. The tubular cylindrical side wall 46a has a trailing end portion 48a and an annular leading end portion 50a.

In accordance with a feature of this embodiment of the invention, the annular leading end portion 50a of the anchor has been sharpened to form a circular point 340. A notch 342 has been formed in the side wall of the anchor. The suture 42a extends into the notch 342.

The suture 42a has an outer leg or section 86a and an inner leg or section 88a. The inner leg or section 88a extends through the passages in the shaft and handle of a suture anchor inserter assembly having the same construction as the suture anchor inserter assembly 30 of FIG. 1. The outer leg or section 86a of the suture 42a extends along the outside of the shaft and into the slot in the handle of the suture anchor inserter assembly.

The sharpened leading end portion 340 of the anchor 40a is effective to cut body tissue. Therefore, force applied against the anchor 40a by the inner member of the shaft of a suture anchor inserter assembly is effective to press the suture anchor into the body tissue. The notch 342 is provided in the sidewall 46a of the anchor to avoid cutting the suture 42a with the relatively sharp leading end portion 340 of the anchor.

Suture Anchor Inserter Assembly—Second Embodiment

In the embodiment of the suture anchor inserter assembly illustrated in FIGS. 1–22, the handle 32 of the suture anchor inserter assembly 30 is advantageously gripped in a manner similar to that in which a pencil is gripped. In the embodiment of the invention illustrated in FIG. 24, the suture anchor inserter assembly is still grasped between the thumb and first two fingers on the hand of the surgeon. However, force is applied against one end of the suture anchor inserter assembly with the palm of the surgeon's hand. Since the embodiment of the invention illustrated in FIG. 24 is generally similar to the embodiment of the invention illustrated in FIGS. 1–22, similar numerals will be utilized to designate similar components, the suffix letter "b" being associated with the numerals of FIG. 24 in order to avoid confusion.

A suture anchor inserter assembly 30b has a handle 32b. A shaft 34b extends axially outward from the handle 32b. Although only a portion of the shaft 34b is shown in FIG. 24, it should be understood that the shaft 34b has the same construction as the shaft 34 of the embodiment of the invention illustrated in FIGS. 1–22.

The handle 32b has a triangular cross-sectional configuration. An end cap 350 encloses the proximal end portion of the handle 32b. The end cap 350 has a generally triangular sleeve portion 352 which covers the recesses 124b and 150b in the sides 56b and 58b of the handle 32b. The end cap 350 has a outer end portion 354 with a configuration corresponding to the configuration of a portion of a sphere. An annular groove 356 is provided to hold excess suture 42b.

When an anchor 40b is to be inserted into body tissue, the anchor is held in a recess at the end of the shaft 34b by the suture 42b in the same manner as previously explained in conjunction with the embodiment of the invention illustrated in FIGS. 1–22. The handle 32b of the suture anchor inserter assembly 30b is gripped with the first two fingers and thumb of the surgeon. The first finger of the surgeon is disposed in engagement with a recess 102b adjacent to the actuator member 94b of a retainer assembly 92b. The outer end section 354 of the end cap 350 is disposed in engagement with the palm of the hand of the surgeon.

The leading end of the anchor 40b is positioned relative to body tissue in the same manner as previously described in conjunction with the embodiment of the invention illustrated in FIGS. 1–22. However, when the anchor is to be pressed into the body tissue, force is applied against the outer end portion 354 of the end cap 350 by the palm of the hand of the surgeon.

Suture Anchor Inserter Assembly—Third Embodiment

In the embodiment of the suture anchor assembly illustrated in FIGS. 1–22, the surgeon controls the depth to which an anchor is inserted by either forming an opening to the desired depth in body tissue or visually monitoring the extent to which the outer member 68 is retracted relative to the inner member 66. In the embodiment of the invention illustrated in FIG. 25, the surgeon selects the desired depth to which the anchor is to be inserted prior to insertion of the anchor. Since the embodiment of the invention illustrated in FIG. 25 is generally similar to the embodiment of the invention illustrated in FIGS. 1–22, similar numerals will be utilized to designate similar components, the suffix "c" being added to the numerals of FIG. 25 to avoid confusion.

A suture anchor inserter assembly 30c has a handle 32c (FIG. 25). A shaft 34c extends axially outward from the handle 32c. An outer or distal end portion 36c has a chamber in which a suture anchor 40c is received. A suture 42c is effected to apply force against the anchor 40c to retain the anchor in the chamber at the distal end portion 36c of the shaft 34c.

The handle 32c has an equilateral triangular cross-sectional configuration. A side 58c of the handle is illustrated in FIG. 25. It should be understood that the handle has two other sides corresponding to the sides 56 and 60 of FIGS. 11 and 13. If desired, the handle 32c could have a cross-sectional configuration other than the preferred triangular cross-sectional configuration.

The shaft 34c is formed by tubular inner and outer members 66c and 68c which are relatively movable. The tubular inner member 66c is fixedly connected with the handle 32c. The tubular inner member 66c has a central passage through which a portion of the suture extends.

The tubular outer member 68c encloses the tubular inner member 66c when the tubular outer member is in the extended position illustrated in FIG. 25. The tubular outer members 68c is axially movable along the inner member from the extended position toward a retracted position. As the tubular outer member 68c moves along the inner member 66c toward a retracted position, the tubular outer member 68c is telescopically retracted into the handle 32c in the manner previously explained in conjunction with the embodiment of the invention (illustrated in FIGS. 1–22).

A retainer assembly 92c is manually operable between an engaged condition (illustrated in FIG. 25) retaining the inner and outer members 66c and 68c against relative movement and a disengaged condition in which the outer member 68c is axially movable relative to the inner member 66c. The retainer assembly 92c includes a manually operable actuator member 94c. The actuator member 94c is manually movable relative to the handle 32c to operate the retainer assembly 92c from the engaged condition to the disengaged condition in the manner previously explained in conjunction with the embodiment of the invention illustrated in FIGS. 1–22.

The side 58c of the handle 34c has a flat major side surface 140c which extends parallel to the central axis of the shaft 34c. The major side surface 140c extends between a corner 108c and a corner 144c. A plurality of ribs 146c extend across the major side surface 140c.

An elongated recess 150c is formed in the major side surface 140c to receive a portion of the suture 42c. A second elongated recess 158c is provided in the second side 58c of the handle 32c. The second recess 158c has a pair of recesses 160c and 162c which engage a detent extending inward from a sidewall of a slide corresponding to the slide 134 of FIGS. 1, 14 and 15.

In accordance with a feature of this embodiment of the invention, a suture anchor insertion depth control assembly 372 (FIG. 25) is provided in association with the inner and outer members 66c and 68c of the shaft 34c. The suture anchor insertion depth control assembly 372 limits the distance which the anchor 40c is inserted into body tissue. Thus, a surgeon can set the insertion depth control assembly 372 to a desired depth of insertion of the suture anchor 40c into body tissue. The suture anchor insertion depth control assembly 372 is then effective to limit the distance which the suture anchor 40c is moved into body tissue by the suture anchor inserter assembly 30c to the desired depth.

The suture anchor insertion depth control assembly 372 includes a stop or control member 374 having an annular configuration. An outer side surface of the control member 374 is disposed in engagement with the inner side surface 216c of the passage 72c through the handle 32c. The circular inner side surface on the annular control or stop member 374 engages and is axially slidable along the outer side surface 214c of the tubular inner member 66c. The position of the control or stop member 374 along the inner member 66c determines the extent of retraction of the outer member 68c into the handle 32c and the depth of insertion of the anchor 40c.

The control member 374 is engageable by a bearing ring 284c on the retainer sleeve (not shown) connected with the outer member 68c. The retainer sleeve which is connected with the outer member 68c has the same construction and is connected with the outer member in the same manner as in which the retainer sleeve 230 is connected with the outer member 68 of the embodiment of the invention illustrated in FIGS. 1–22. Therefore, engagement of the bearing ring 284c with the control or stop member 374 limits the extent of retraction of the outer member 68c into the handle 32c.

A control or index rod 378 is connected with the control or stop member 374. The control or index rod 378 has an end portion 380 which extends through a slot 382 in the side 58c of the handle 32c. The slot 382 is provided with a plurality of notches or index locations which are engaged by the end portion 380 of the index rod 378 to retain the index rod and the stop member 374 against movement relative to the handle.

When the end portion 380 of the index rod 378 is disengaged from the notches 386, the index rod and the stop member 374 can be moved axially along the central passage 72c through the handle 32c. As this occurs, the stop member 374 slides along the cylindrical outer side surface 214c of the inner member 66c. Since the position of the stop member 374 relative to the inner member 66c determines the distance which the outer member 68c can be retracted into the handle 32c, the location of the stop member determines the extent to which the inner member 66c and anchor 40c can be inserted into body tissue.

When the anchor 40c is to be inserted into the body tissue, the surgeon moves the end portion 380 of the index rod 378 along the slot 382 to a notch 386 corresponding to the desired depth to which the anchor 40c is to be inserted in the body tissue. Suitable indicia is provided adjacent to each of the notches 386 to provide an indication of the depth to which the suture anchor 40c is to be inserted into body tissue.

When the end portion 380 of the index rod 376 has been moved to a location opposite to a notch 386 corresponding to a desired depth of insertion of the suture anchor 40c into body tissue, the end portion 380 of the index rod 378 is moved into the selected notch. As the end portion 380 of the index rod 378 is moved along the slot 382 into alignment with the selected notch 386, the control member 374 is either pushed or pulled along the inner member 66c. Once the end portion 380 of the index rod 378 moves into one of the notches 386, the index rod 378 and stop member 374 are held against movement relative to the inner member 66c.

After the end portion 380 has been moved into engagement with a notch 386 corresponding to the selected insertion depth for the anchor 40c and after the shaft 34c has been positioned relative to body tissue, the actuator member 94 is manually depressed. This releases the outer member 68c, in the manner previously explained, for telescopic sliding movement along the inner member 66c. As the anchor 40c is moved into body tissue, the body tissue presses against the leading end of the outer member 68c and slides the outer member 68c along the inner member 66c into the handle 32c. As the outer member 68c is retracted into the handle 32c, the annular stop surface 292c on the bearing ring 284c moves toward the stop member 374.

When the anchor 40c has been inserted into the body tissue for the desired distance, the stop surface 292c engages the stop member 274. The stop member 374 is then effective to block further movement of the outer member 68c relative to the inner member 66c. At this time, the anchor 40c will have been moved into body tissue to a depth corresponding to the setting of the end portion 380 of the index rod 378.

Suture Anchor Inserter Assembly—Fourth Embodiment

In the embodiment of the suture anchor inserter assembly 30 illustrated in FIGS. 1–22, the shaft 44 of the suture anchor inserter assembly 30 has a linear configuration. In the embodiment of the invention illustrated in FIG. 26, the shaft of the suture anchor inserter assembly has a non-linear configuration to facilitate positioning of a suture anchor in difficult to reach locations. Since the embodiment of the invention illustrated in FIG. 26 is generally similar to the embodiment of the invention illustrated in FIGS. 1–22, similar numerals will be utilized to designate similar components, the suffix "d" being associated with the numerals of FIG. 26 to avoid confusion.

The suture anchor inserter assembly 30d includes a manually engageable handle 32d having a triangular cross-sectional configuration. A shaft 34d extends axially outward from the handle. An outer or distal end portion 36d of the shaft 34d has a chamber in which a suture anchor 40d is received. A suture 42d is effective to apply force against the anchor 40d to retain the anchor in the chamber at the distal end portion 36d of the shaft 34d.

The handle 32d has a flat side 58d. In addition, the handle has two other flat sides, corresponding to the sides 56 and 60 of FIGS. 11 and 13. The three sides of the handle 32d are arranged in a triangular array in the manner previously explained in conjunction with the embodiment of the invention illustrated in FIGS. 1–22.

The tubular inner member 66d of the shaft 34d has a central passage with an inner end portion which is axially aligned with a central passage through the handle 32d. The suture 42d extends through the passage in the inner member 66d and the passage in the handle 32d. The tubular inner member 66d has an inner end portion which is fixedly connected with the handle 32d. The tubular outer member 68d is axially movable along the inner member 66d from the extended position shown in FIG. 26 to a retracted position in which the outer member 66d extends into the handle 32d.

A retainer assembly 92d is manually operable between an engaged condition (FIG. 26) retaining the inner and outer members 66d and 68d against relative movement and a disengaged condition in which the outer member 68d is slidably movable along the inner member 66d. As the outer member 68d is moved along the inner member 66d from the extended position of FIG. 26, the outer member is telescopically retracted into the handle 32d.

The retainer assembly 92d includes a manually operable actuator member 94d. The actuator member 94d is slidably mounted on the handle 32d. The actuator member 94d is manually movable relative to the handle between the engaged position of FIG. 26 and disengaged position to release the outer member 68d for movement relative to the inner member 66d in the manner previously explained in conjunction with the embodiment of the invention illustrated in FIGS. 1–22.

In accordance with a feature of the embodiment of this invention, the tubular inner member 66d has an outer end portion 400 which has an arcuate longitudinal central axis. Thus, the outer end portion 400 of the inner member 66d is formed as a portion of a circle.

In order to accommodate movement of the outer member 68d relative to the inner member 66d, the outer member 68d has an outer end portion 404 which is flexible and encloses the outer portion 400 of the inner member 66d when the outer member is in the extended position. Upon movement of the outer member 68d from the extended position shown in FIG. 26 to a retracted position, the flexible outer end portion 404 of the outer member 68d moves along a straight inner portion 406 of the inner member 66d. As this occurs, the portion of the flexible outer end portion 404 of the outer member 68d is straightened from the arcuate configuration of FIG. 26 to a linear configuration.

The outer portion 404 of the outer member 68d may be formed of a flexible metallic tubing, i.e., stainless steel tubing. The flexible metallic tubing would have a series of closely spaced joints which enable the tubing to freely bend to the configuration of the outer end portion 400 of the inner member 66d. Alternatively, the outer end portion 404 of the outer member 68d may be formed of a flexible polymeric tubing.

Conclusion

In view of the foregoing description, it is apparent that the present invention relates to a new and improved suture anchor inserter assembly 30 (FIG. 1) and method of using the suture anchor inserter assembly. The suture anchor inserter assembly 30 includes a handle 32 and a shaft 34 which extends outward from the handle. The shaft 34 may have a linear or non-linear configuration (FIGS. 1 and 26). A suture 42 may extend through a passage 70, 72 in the shaft 34 and the handle. The suture 42 may be used to apply force to an anchor 40 to hold the anchor in a chamber 38 at an outer end 36 of the shaft 34.

The shaft 34 may advantageously be formed by relatively movable inner and outer members 66 and 68. A retainer assembly 92 may hold the inner and outer members 66 and 68 against relative movement until the anchor 40 has been moved to a desired position relative to body tissue. Moving the anchor 40 to a desired position relative to body tissue may be facilitated by deflecting body tissue with the shaft 34 of the suture anchor inserter assembly 30 (FIG. 17).

Once the anchor 40 has been moved to the desired position relative to the body tissue, the retainer assembly 92 is manually actuated to release the inner and outer members 66 and 68 for relative movement. During this relative movement, the anchor 40 is inserted into either hard or soft body tissue.

In one embodiment of the invention, the outer member 68 is movable relative to the inner member 66 upon operation of the retainer assembly 92 to a release condition. As the outer member 68 is moved relative to the inner member 66, the outer member is advantageously moved into the handle 32. To facilitate gripping of the handle 32, the handle may advantageously have a triangular cross-sectional configuration.

The suture anchor inserter assembly 30 may advantageously include a suture anchor insertion depth control assembly 372 (FIG. 25). The suture anchor insertion depth control assembly 372 is operable to limit the distance to which an anchor 40c is inserted into body tissue.

Having described the invention, the following is claimed:

1. An apparatus for use in positioning a suture anchor relative to body tissue, said apparatus comprising a handle, an inner member having a first end portion fixedly connected with said handle and a second end portion spaced from said handle, and a tubular outer member at least partially enclosing said inner member, said outer member being slidable along said inner member into said handle in a direction parallel to a longitudinal central axis of said inner member, said outer member being slidable along said inner member into said handle to move said outer member from an extended position in which said outer member extends beyond said second end portion of said inner member to a retracted position in which said second end portion of said inner member extends beyond said outer member, said inner and outer members cooperating to form a chamber for receiving the suture anchor when said outer member is in the extended position.

2. An apparatus as set forth in claim 1 wherein a first length of said inner member and a first length of said outer member are disposed in said handle in a telescopic relationship when said outer member is in the extended position, a second length of said inner member and a second length of said outer member being disposed in said handle in a telescopic relationship when said outer member is in the retracted position, said second length of said inner member and said second length of said outer member being longer than said first length of said inner member and said first length of said outer member so that the extent of the telescopic relationship in said handle between said inner and outer members is greater when said outer member is in the retracted position than when said outer member in the extended position.

3. An apparatus as set forth in claim 1 wherein a first length of said outer member is enclosed by said handle when said outer member is in the extended position and a second length of said outer member is enclosed by said handle when said outer member is in the retracted position, said second length of said outer member being longer than said first length of said outer member.

4. An apparatus as set forth in claim 1 wherein said handle has a leading end portion, said outer member extends a first distance outward from said leading end portion of said handle when said outer member is in the extended position, said outer member extends a second distance outward from said leading end portion of said handle when said outer member is in the retracted position, said second distance being less than said first distance.

5. An apparatus as set forth in claim 4 wherein said inner member extends outward from said leading end portion of said handle for a third distance, said third distance being less than said first distance and greater than said second distance.

6. An apparatus as set forth in claim 1 wherein said second end portion of said inner member has surface means for applying force transmitted from said handle through said inner member to a trailing end of the suture anchor to move the suture anchor into body tissue as said outer member slides along said inner member into said handle.

7. An apparatus as set forth in claim 1 wherein said inner member has surface means for defining a passage which receives a suture which extends through the anchor, said passage in said inner member extends between said first and second end portions of said inner member.

8. An apparatus as set forth in claim 1 further including surface means connected with said tubular outer member for engaging body tissue and transmitting force between the body tissue and said tubular outer member to effect movement of said tubular outer member into said handle.

9. An apparatus as set forth in claim 1 further including means connected with said outer member for limiting the extent of movement of said outer member into said handle.

10. An apparatus as set forth in claim 1 further including a retainer member disposed on said handle and movable relative to said handle between a retaining position in which said retainer member is effective to retain said outer member in the extended position and a release position in which said retainer member is ineffective to retain said outer member in the extended position.

11. An apparatus as set forth in claim 10 wherein said retainer member includes surface means which is engageable with a portion of a suture connected with the anchor to retain the engaged portion of the suture against movement relative to said handle when said retainer member is in the retaining position.

12. An apparatus as set forth in claim 10 wherein said handle includes a guide surface along which said retainer member is movable between the retaining and release positions, said guide surface being effective to guide movement of the retainer member along a path having a central axis which extends transverse to a central axis of said outer member.

13. An apparatus as set forth in claim 10 wherein said retainer member has a manually engageable end portion against which force is manually applied to move said retainer member from the retaining position to the release position.

14. An apparatus as set forth in claim 10 further including first and second stop surfaces connected with said outer member, said first and second stop surfaces being spaced from each other along a central axis of said outer member, said retainer member being disposed adjacent to said first stop surface when said outer member is in the extended position, said retainer member being disposed adjacent to said second stop surface when said outer member is in the retracted position.

15. An apparatus as set forth in claim 10 wherein said retainer member includes an opening through which a central axis of said outer member extends, said opening being movable transversely to the central axis of said outer member upon movement of said retainer member between the retaining and release positions, the central axis of said outer member extends through a first portion of the opening in said retainer member when said retainer member is in the retaining position, the central axis of said outer member extends through a second portion of the opening in said retainer member when said retainer member is in the release position.

16. An apparatus as set forth in claim 10 wherein said handle includes three longitudinally extending sides disposed in a triangular array with longitudinal axes of said sides extending parallel to a central axis of said inner member, said retainer member projects from one of said sides of said handle when said retainer member is in the retaining position.

17. An apparatus as set forth in claim 1 wherein said handle includes three longitudinally extending sides disposed in a triangular array having a central axis which is parallel to central axes of said inner and outer members.

18. An apparatus as set forth in claim 17 wherein a first one of said longitudinally extending sides of said handle includes surface means for defining a slot which receives a portion of a suture, said slot having a longitudinal central axis which extends parallel to a longitudinal central axis of said outer member.

19. An apparatus as set forth in claim 18 wherein a second one of said longitudinally extending sides of said handle includes surface means for defining a recess which receives a needle connected with the suture.

20. An apparatus as set forth in claim 19 wherein a third one of said longitudinally extending sides of said handle includes surface means for defining a recess for receiving a portion of the suture.

21. An apparatus as set forth in claim 17 wherein said longitudinally extending sides of said handle are interconnected by a plurality of longitudinally extending corner portions having axes which extend parallel to the longitudinal central axis of said inner member, said longitudinally extending sides of said handle intersect at said corner portions of said handle, a first one of said longitudinally extending sides of said handle including a first plurality of ribs which extend between a first one of said corner portions and a second one of said corner portions, a second one of said longitudinally extending sides of said handle including a second plurality of ribs which extend between said second one of said corner portions and a third one of said corner portions.

22. An apparatus as set forth in claim 1 wherein said chamber has a maximum axial extent when said outer member is in the extended position, said chamber having an axial extent which is less than the axial extent of the suture anchor when said outer member is in the extended position, said second end portion of said inner member cooperates with said outer member to form an end of said chamber which is engageable by a trailing end of the suture anchor when the suture anchor is in said chamber with a leading end of the suture anchor outside of said chamber and with said outer member in the extended position.

23. An apparatus as set forth in claim 1 wherein said outer member extends a first distance into said handle when said outer member is in the extended position, said outer member extends a second distance into said handle when said outer member is in the retracted position, said second distance being greater than said first distance.

24. An apparatus as set forth in claim 1 further including means for limiting the depth to which an anchor is to be inserted into body tissue to a selected one of a plurality of depths, said means for limiting the depth to which an anchor is to be inserted into body tissue includes means for limiting the distance which said outer member moves along said inner member from the extended position to the retracted position to a selected one of a plurality of distances.

25. An apparatus as set forth in claim 24 wherein said means for limiting the depth to which an anchor is inserted into body tissue includes depth indicator means disposed on said handle for indicating the depth to which an anchor is to be inserted into body tissue.

26. An apparatus as set forth in claim 1 wherein said inner and outer members have a nonlinear longitudinal configuration, at least a portion of said outer member being flexible to accommodate movement of said outer member along a nonlinear portion of said inner member.

27. An apparatus comprising a handle, an inner member having a first end portion connected with said handle and a second end portion spaced from said handle, an outer member which at least partially encloses said inner member, a suture anchor partially enclosed by said outer member, said suture anchor having a trailing end which is disposed in engagement with said second end portion of said inner member and which is enclosed by said outer member, said suture anchor having a leading end opposite from said trailing end, said leading end of said suture anchor being disposed outward of an outer end of said outer member, and a suture having a first portion extending axially through said handle, inner and outer members and suture anchor, said suture having a second portion which extends along an outer side surface of said outer member, said first and second portions of said suture being effective to transmit force which is applied against the leading end of said suture anchor to press the trailing end of said suture anchor against said second end portion of said inner member.

28. An apparatus as set forth in claim 27 wherein said first end portion of said inner member is fixedly connected with said handle, said outer member being slidable along said inner member into said handle.

29. An apparatus as set forth in claim 27 wherein said anchor projects from said second end portion of said outer member.

30. An apparatus as set forth in claim 27 further including a needle connected with said second portion of said suture, said handle including surface means for defining a recess for receiving said needle.

31. An apparatus as set forth in claim 27 wherein said handle includes three longitudinally extending sides disposed in a triangular array, said second portion of said suture extends into said handle through an opening formed in one of said longitudinally extending sides of said handle.

32. An apparatus as set forth in claim 27 wherein one of said inner and outer members is movable relative to said handle, said apparatus further including a retainer connected with said handle, said retainer being movable relative to said handle between a first position in which said retainer is effective to retain said one of said inner and outer members against movement relative to said handle and a second position in which said retainer is ineffective to retain said one of said inner and outer members against movement relative to said handle.

33. An apparatus as set forth in claim 32 further including first and second stop surfaces which are spaced from each other and are connected with said one of said inner and outer members, said retainer being engageable with said first stop surface to limit movement of said one of said inner and outer members in a first direction relative to said handle, said retainer engageable with said second stop surface to limit movement of said one of said inner and outer members in a second direction relative to said handle.

34. An apparatus for use in positioning a suture anchor relative to body tissue, said apparatus comprising a handle, an inner member having a first end portion connected with said handle and a second end portion which is spaced from said handle, said second end portion of said inner member being engageable with the anchor, an outer member at least partially enclosing said inner member, said outer member having a first end portion connected with said handle and a second end portion which is spaced from said handle, said outer member having an inner surface which at least partially encloses the anchor prior to positioning of the anchor in body tissue, one of said inner and outer members being movable relative to the other of said inner and outer members during positioning of the anchor in body tissue, and an actuator connected with said handle, said actuator being movable relative to said handle between a first position in which said one of said inner and outer members is retained against movement relative to the other of said inner and outer members and a second position in which said one of said inner and outer members is movable relative to the other of said inner and outer members during positioning of the anchor in body tissue.

35. An apparatus as set forth in claim 34 wherein said actuator has a surface which is manually engageable to move said actuator from the first position to the second position.

36. An apparatus as set forth in claim 34 wherein said inner and outer members cooperate to at least partially define a chamber which receives a trailing end portion of the anchor and from which a leading end portion of the anchor extends when said actuator is in the first position.

37. An apparatus as set forth in claim 34 wherein said second end portion of said inner member is enclosed by said outer member when said actuator is in the first position, said inner member and said outer member being movable relative to each other to a position in which said second end portion of said inner member extends from said second end portion of said outer member when said actuator is in the second position.

38. An apparatus as set forth in claim 34 wherein said actuator has an opening with a first portion having a first configuration and a second portion having a second configuration, said actuator being manually movable from the first position in which a central axis of said one of said inner and outer members extends through the first portion of the opening in said actuator to the second position in which the central axis of said one of said inner and outer members extends through the second portion of the opening in said actuator to release said one of said inner and outer members for movement relative to the other of said inner and outer members.

39. An apparatus as set forth in claim 34 further including a guide surface disposed on said handle for guiding movement of said actuator between the first and second positions, said actuator having a manually engageable surface against which force is manually applied to move said actuator along said guide surface from the first position to the second position.

40. An apparatus as set forth in claim 34 further including first and second stop surfaces connected with said one of said inner and outer members, said actuator being disposed adjacent to said first stop surface when said one of said inner and outer members is in a first position relative to said other of said inner and outer members, said second stop surface being spaced from said actuator when said one of said inner and outer members is in the first position relative to said other of said inner and outer members, said actuator being disposed adjacent to said second stop surface when said one of said one of said inner and outer members is in a second position relative to said other of said inner and outer members, said first stop surface being spaced from said actuator when said one of said inner and outer members is in the second position relative to said other of said inner and outer members.

41. An apparatus as set forth in claim 40 wherein said second end portion of said inner member has surface means for applying force transmitted through said inner member to a trailing end of the anchor to move the anchor into body tissue upon movement of said one of said inner and outer members from the first position to the second position.

42. An apparatus as set forth in claim 40 wherein said actuator has an opening with first and second portions, said actuator being manually movable from the first position to the second position while said one of said inner and outer members is in the first position of said one of said inner and outer members relative to said other of said inner and outer members and while said actuator is adjacent to said first stop surface, said one of said inner and outer members having a central axis which extends through the first portion of the opening in said actuator when said actuator is in the first position of said actuator, said central axis of said one of said inner and outer members extends through the second portion of the opening in said actuator when said actuator is in the second position of said actuator.

43. An apparatus as set forth in claim 34 wherein said first end portion of said inner member is fixedly connected with said handle, said outer member is said one of said inner and outer members and is slidable along said inner member to move said outer member from an extended position in which said outer member extends beyond said second end portion of said inner member to a retracted position in which said second end portion of said inner member extends beyond said second end portion of said outer member.

44. An apparatus as set forth in claim 34 wherein said inner member has surface means for defining a passage which receives a suture which extends through the anchor, said passage in said inner member extends between said first and second end portions of said inner member.

45. An apparatus as set forth in claim 34 wherein said second end portion of said one of said inner and outer members has surface means for engaging body tissue and transmitting force between the body tissue and said one of said inner and outer members to effect movement of said one of said inner and outer members relative to said other of said inner and outer members.

46. An apparatus as set forth in claim 34 wherein said handle includes three longitudinally extending sides disposed in a triangular array having a central axis which is parallel to central axes of said inner and outer members.

47. An apparatus as set forth in claim 34 wherein said handle includes surface means for defining a slot which extends between axially opposite end portions of said handle and which receives a portion of a suture which extends through the slot between said axially opposite end portions of said handle, said slot having a longitudinal central axis which extends parallel to a longitudinal central axis of said outer member.

48. An apparatus as set forth in claim 34 wherein said actuator includes surface means for engaging a portion of a suture connected with the anchor when said actuator is in the first position to retain at least the portion of the suture engaged by the actuator against movement relative to said handle.

49. An apparatus as set forth in claim 34 further including a stop member disposed on said handle and movable between a first stop position and a second stop position, said stop member being effective to limit movement of said one of said inner and outer members to a first distance when said actuator is in the second position of said actuator and said stop member is in the first stop position of said stop member, said stop member being effective to limit movement of said one of said inner and outer members to a second distance when said actuator is in the second position of said actuator and said stop member is in the second stop position of said stop member, said second distance being greater than said first distance.

50. An apparatus as set forth in claim 49 further including means movable relative to said handle to move said stop member between said first and second stop positions.

51. An apparatus as set forth in claim 49 further including indicia disposed on said handle for indicating when said stop member is in the first stop position and for indicating when said stop member is in the second stop position.

52. An apparatus as set forth in claim 34 wherein said second end portion of said inner member has a curving configuration and said first end portion of said inner member has a linear configuration, said second end portion of said outer member has a curving configuration corresponding to the curving configuration of said second end portion of said inner member and said first end portion of said outer member has a linear configuration, at least a portion of the second portion of said one of said inner and outer members being flexible to facilitate movement of said one of said inner and outer members relative to the other of said inner and outer members.

53. A method of positioning a suture anchor relative to body tissue, said method comprising the steps of moving the anchor into engagement with body tissue by transmitting force from a handle through an inner member to the anchor while the inner member and anchor are at least partially enclosed by an outer member, and, thereafter, retracting the outer member into the handle while maintaining the inner member stationary relative to the handle.

54. A method as set forth in claim 53 further including the step of moving the anchor and inner member into the body tissue under the influence of force transmitted from the handle through the inner member to a trailing end of the anchor while retracting the outer member into the handle and maintaining the inner member stationary relative to the handle.

55. A method as set forth in claim 53 wherein said step of retracting the outer member into the handle is performed under the influence of force applied against the outer member by the body tissue and includes sliding the outer member along an outer side surface of the inner member.

56. A method as set forth in claim 53 wherein said step of moving the anchor into engagement with body tissue is performed with a portion of the outer member enclosed by the handle and a portion of the outer member extending from the handle, said step of retracting the outer member into the handle includes increasing the axial extent of the portion of the outer member enclosed by the handle and decreasing the axial extent of the portion of the outer member extending from the handle.

57. A method as set forth in claim 53 wherein said step of moving the anchor into engagement with body tissue is performed with a leading end portion of the anchor extending ahead of a leading end of the outer member and with a trailing end portion of the anchor enclosed by the outer member and while maintaining the anchor stationary relative to the inner and outer members.

58. A method as set forth in claim 53 wherein said step of moving the anchor into engagement with body tissue is performed with a portion of a suture extending through the anchor, inner member and handle.

59. A method as set forth in claim 53 further including the steps of selecting a desired depth of insertion of the anchor into body tissue and interrupting said step of retracting the outer member into the handle upon insertion of the anchor to the desired depth in body tissue.

60. A method as set forth in claim 53 further including the step of moving a depth control member along the handle to a position which corresponds to a desired depth of insertion of the anchor into body tissue and interrupting said step of retracting the outer member into the handle upon retraction of the outer member into the handle through a distance which corresponds to the position of the depth control member.

61. A method as set forth in claim 53 further including the steps of moving a step member along the inner member to a position which corresponds to a desired depth of insertion of the anchor into body tissue prior to moving the anchor into engagement with body tissue, and blocking retraction of said outer member into the handle with the stop member upon insertion of the anchor to the desired depth into body tissue.

62. A method of positioning a suture anchor relative to body tissue, said method comprising the steps of manually gripping a handle having an inner member extending from the handle and having an outer member enclosing at least a portion of the inner member and at least a portion of the anchor, moving the outer member into engagement with body tissue while retaining the inner and outer members against movement relative to each other and to the handle, enabling relative movement to occur between the inner and outer members by manually moving an actuator member relative to the handle, and, thereafter, moving the anchor relative to the body tissue by moving one of the inner and outer members relative to the other of the inner and outer members.

63. A method as set forth in claim 62 wherein said step of enabling relative movement to occur between the inner and outer members by manually moving the actuator member relative to the handle includes disengaging the actuator member from a stop surface connected with said one of said inner and outer members to enable said one of said inner and outer members to move relative to said other of the inner and outer members.

64. A method as set forth in claim 62 wherein said step of moving the outer member into engagement with body tissue includes gripping a portion of a suture which engages the anchor with said actuator member to hold the gripped portion of the suture against movement relative to the handle.

65. A method as set forth in claim 62 wherein said step of moving the anchor relative to the body tissue by moving one of the inner and outer members relative to the other of said inner and outer members includes moving said one of said inner and outer members along a path which extends through the actuator member.

66. A method as set forth in claim 62 wherein said step of moving the anchor relative to the body tissue by moving one of the inner and outer members relative to the other of said inner and outer members includes decreasing a distance between an outer end of the outer member and the handle while maintaining a distance between an outer end of the inner member and the handle constant.

67. A method as set forth in claim 66 wherein said step of moving the anchor relative to the body tissue by moving one of the inner and outer members relative to the other of the inner and outer members includes moving the outer member relative to the inner member under the influence of force applied against the outer member by the body tissue.

68. A method as set forth in claim 62 wherein said step of moving the anchor relative to the body tissue by moving one of the inner and outer members relative to the other of the inner and outer members includes moving a portion of the outer member into the handle while maintaining the inner member stationary relative to the handle.

69. A method of positioning a suture anchor relative to body tissue, said method comprising the steps of selecting a depth of insertion of the anchor into body tissue, said step of selecting a depth of insertion of an anchor into body tissue includes positioning a depth control member relative to at least one of an inner member and an outer member which at least partially encloses the inner member, moving the anchor into body tissue by applying force against the anchor with the inner member and effecting relative movement between the inner and outer members, and blocking relative movement between the inner and outer members with the depth control member upon movement of the anchor into the body tissue through a distance corresponding to the selected depth of insertion of the anchor into body tissue.

70. A method as set forth in claim 69 wherein said step of positioning a depth control member relative to at least one of an inner member and an outer member which at least partially encloses the inner member includes sliding the depth control member along the one of the inner and outer members to a selected position relative to the one of the inner and outer members.

71. A method as set forth in claim 69 wherein said step of applying force against the anchor with the inner member includes transmitting force from a handle to the inner member, said step of positioning a depth control member relative to at least one of an inner member and an outer member which at least partially encloses the inner member includes moving the depth control member relative to the handle.

72. A method as set forth in claim 71 wherein said step of effecting relative movement between the inner and outer members includes retracting the outer member into the handle while maintaining the inner member stationary relative to the handle.

73. An apparatus for use in positioning a suture anchor relative to body tissue, said apparatus comprising a handle, and an elongated shaft portion extending axially outward from said handle, said handle having a first longitudinally extending side, said first longitudinally extending side of said handle having first and second longitudinally extending edge portions, said handle having a second longitudinally extending side, said second longitudinally extending side of said handle having first and second longitudinally extending edge portions, said first longitudinally extending edge portion of said second side of said handle being connected with said second longitudinally extending edge portion of said first side of said handle to form a first corner portion of said handle, said handle having a third longitudinally extending side, said third longitudinally extending side of said handle having first and second longitudinally extending edge portions, said first longitudinally extending edge portion of said third side of said handle being connected with said second longitudinally extending edge portion of said second side of said handle to form a second corner portion of said handle, said second longitudinally extending edge portion of said third side of said handle being connected with said first longitudinally extending edge portion of said first side of said handle to form a third corner portion of said handle, said handle having a central axis which is parallel to a central axis of said shaft portion, said shaft portion being partially disposed in said handle.

74. An apparatus as set forth in claim 73 wherein said shaft portion has a longitudinally extending central passage which extends through said shaft portion and is axially aligned with a passage which extends through said handle, said passage in said shaft portion having an enlarged portion in which the anchor is disposed with a suture extending through a central passage in the anchor, through the passage in said shaft portion and through the passage in said handle.

75. An apparatus as set forth in claim 74 wherein said first longitudinally extending side of said handle includes surface means for defining a first plurality of ribs which extend across said first longitudinally extending side of said handle between said first and third corner portions in a direction transverse to a longitudinal central axis of said first longitudinally extending side of said handle, said first plurality of ribs being engageable by a thumb on a hand of a person manually gripping said handle, said third longitudinally extending side of said handle includes surface means for defining a second plurality of ribs which extend across said third longitudinally extending side of said handle between said second and third corner portions in a direction transverse to a longitudinal central axis of said third longitudinally extending side of said handle, said second plurality of ribs being engageable by a finger on the hand of the person manually gripping said handle.

76. An apparatus as set forth in claim 75 wherein said second longitudinally extending side of said handle includes surface means for defining an elongated recess having a central axis which extends parallel to a longitudinal central axis of said second longitudinally extending side of said handle, said elongated recess being engageable by a finger on the hand of the person manually gripping said handle.

77. An apparatus as set forth in claim 76 wherein said second longitudinally extending side of said handle includes surface means for defining a third plurality of ribs which extend across said second longitudinally extending side of said handle between said first and second corner portions in a direction transverse to the longitudinal central axis of said second longitudinally extending side of said handle, said elongated recess having a first and second end portions, said first end portion of said elongated recess being disposed closer to an end of said handle from which said shaft portion extends than said second end portion of said elongated recess, said third plurality of ribs being disposed adjacent to said first end portion of said elongated recess.

78. An apparatus as set forth in claim 73 wherein said shaft portion includes an inner member, an outer member which at least partially encloses said inner member, said inner and outer members being relatively movable to move the anchor relative to body tissue, said apparatus further including an actuator disposed on said handle, said actuator being movable relative to said handle by a finger on the hand of a person manually gripping the handle, said actuator being movable between a first position in which said inner and outer members are held against relative movement and a second position in which said inner and outer members are relatively movable.

79. An apparatus as set forth in claim 73 wherein said handle includes surface means for defining a slot which extends into said handle from one of said longitudinally extending sides of said handle to enclose a portion of a length of a suture extending from the anchor, said slot having a central axis which extends parallel to the central axis of said shaft portion.

80. An apparatus as set forth in claim 73 wherein said longitudinally extending sides includes surface means for defining a recess to receive a needle connected with a suture, said apparatus further including a member which partially encloses said handle and is movable relative to said handle between a closed position at least partially blocking said recess and an open position in which said member is ineffective to block said recess, said member having a first side wall which overlies a portion of said first longitudinally extending side of said handle, a second side wall which overlies a portion of said second longitudinally extending side of said handle, a first corner portion which interconnects said first and second side walls of said member and extends along said first corner portion of said handle, a third side wall which overlies a portion of said third longitudinally extending side of said handle, a second corner portion which interconnects said second and third side walls of said member and extends along said second corner portion of said handle, one of said side walls of said member being disposed across said recess when said member is in the closed position.

81. An apparatus as set forth in claim 80 wherein said member further includes a third corner portion which interconnects said first and third side walls of said member and extends along said third corner portion of said handle.

82. An apparatus as set forth in claim 80 wherein said handle includes surface means for defining a slot which extends into said handle from to enclose a portion of a length of a suture extending from the anchor, said slot having a central axis which extends parallel to the central axis of said shaft portion, said member having surface means for defining an opening which extends through said member and extends between opposite ends of said member, said opening being aligned with said slot to enable a portion of the suture to move through said opening into said slot.

83. An apparatus as set forth in claim 80 wherein said member has an end surface which extends across one end of said handle to enable force to be applied against said member by a palm on a hand of a person manually gripping said handle.

84. An apparatus as set forth in claim 73 wherein said handle has a triangular cross sectional configuration as viewed in a plane extending perpendicular to the central axis of said shaft portion, said handle having a longitudinal central axis which is coincident with the central axis of said shaft portion.

85. An apparatus as set forth in claim 73 wherein said handle has an equilateral triangular cross sectional configuration as viewed in a plane extending perpendicular to the central axis of said shaft portion.

86. An apparatus as set forth in claim 73 wherein said first, second and third longitudinally extending sides of said handle are disposed in a triangular array.

87. An apparatus as set forth in claim 73 wherein at least a portion of said shaft portion is movable relative to said handle between an extended position in which said portion of said shaft portion extends outward from said handle and a retracted position in which said portion of said shaft portion is disposed in said handle.

88. A method comprising the steps of providing a suture anchor inserter having a handle with a shaft portion extending outward from the handle and an anchor disposed in the shaft portion with a suture extending through the anchor, moving the shaft portion of the inserter into body tissue along an insertion path, thereafter, displacing first body tissue in a direction transverse to a longitudinal central axis of the insertion path, said step of displacing the first body tissue includes moving the first body tissue after having performed said step of moving the shaft portion of the inserter into body tissue, said step of moving the first body tissue includes moving the first body tissue from a first position to a second position relative to second body tissue by applying force against the first body tissue with the shaft portion of the inserter, said step of applying force against the first body tissue includes manually applying force to the handle of the inserter in a direction transverse to a central axis of the inserter and transmitting the manually applied force from the handle of the inserter to the shaft portion of the inserter, and, thereafter, moving the anchor into the second body tissue under the influence of force applied against the anchor by the shaft portion of the inserter, said step of moving the anchor into the second body tissue being performed while the first body tissue is blocked against movement back to the first position by the shaft portion of the inserter.

89. A method as set forth in claim 88 wherein said step of applying force against the first body tissue includes pressing an outer side surface on an outer member which is part of the shaft portion against the first body tissue, said step of moving the anchor into the second body tissue includes moving an inner member which is part of the shaft portion relative to the outer member to thereby tend to minimize relative movement between the outer member and the first body tissue as the anchor is moved into the second body tissue.

90. A method as set forth in claim 88 further including applying force to the first body tissue with the suture after having performed said step of moving the anchor into the second body tissue.

91. A method as set forth in claim 88 wherein said step of moving the anchor into the second body tissue includes perforating an imperforate surface on the second body tissue with a leading end of the anchor.

92. A method as set forth in claim 88 wherein said step of displacing the first body tissue is performed with a trailing end portion of the anchor enclosed by the shaft portion of the inserter and with a leading end portion of the anchor extending from the shaft portion of the inserter, said step of moving the anchor into the second body tissue includes engaging the second body tissue with the leading end portion of the anchor while the trailing end portion of the anchor is enclosed by the shaft portion of the inserter.

93. A method as set forth in claim 88 wherein the shaft portion of the inserter includes inner and outer members which cooperate to form a chamber in which at least a portion of the anchor is disposed, said method further including the steps of retaining the inner and outer members against movement relative to the handle of the inserter while performing said step of applying force against the first body tissue, and manually moving an actuator member relative to the handle to release one of the inner and outer members for movement relative to the handle during performance of said step of moving the anchor into the second body tissue, said step of moving the anchor into the second body tissue includes moving the one of the inner and outer members relative to the handle.

94. A method as set forth in claim 93 wherein said step of moving the anchor into the second body tissue includes moving the outer member into the handle under the influence of force applied against the outer member by the second body tissue.

95. An apparatus for use in positioning a suture anchor in body tissue, said apparatus comprising a handle, said handle including surface means for at least partially defining a passage extending through said handle, a tubular inner member having a first end portion disposed in the passage in said handle and a second end portion spaced from said handle, said inner member having surface means defining a passage which extends axially through said inner member and is coaxial with the passage in said handle, a tubular outer member at least partially enclosing said inner member, said inner and outer members cooperating to form a chamber for receiving the anchor with a suture extending from the anchor through the passages in said handle and said inner member, said inner and outer members being relatively movable to eliminate the chamber and effect movement of the anchor into body tissue with the suture extending through the passages in said handle and said inner member, and a sleeve which extends around and is axially movable along said handle, said sleeve having an inner side surface which engages said handle and an outer side surface opposite from said inner side surface, said sleeve having a first end surface which faces toward said second end portion of said tubular inner member and a second end surface which faces away from said second end portion of said tubular inner member, said inner and outer side surfaces on said sleeve extend between said first and second end surfaces on said sleeve, said sleeve includes surface means for defining a first opening which extends along said sleeve between said first and second end surfaces on said sleeve and extends between said inner and outer side surfaces on said sleeve, said handle including surface means for defining a second opening into which a portion of the suture is movable through the first opening in said sleeve.

96. An apparatus as set forth in claim 95 wherein said handle has a first longitudinally extending side, said first longitudinally extending side of said handle having first and second longitudinally extending edge portions, said handle having a second longitudinally extending side, said second longitudinally extending side of said handle having first and second longitudinally extending edge portions, said first longitudinally extending edge portion of said second side of said handle being connected with said second longitudinally extending edge portion of said first side of said handle to form a first corner portion of said handle, said handle having a third longitudinally extending side, said third longitudinally extending side of said handle having first and second longitudinally extending edge portions, said first longitudinally extending edge portion of said third side of said handle being connected with said second longitudinally extending edge portion of said second side of said handle to form a second corner portion of said handle, said second longitudinally extending edge portion of said third side of said handle being connected with said first longitudinally extending edge portion of said first side of said handle to form a third corner portion of said handle, said sleeve having a first side wall which overlies a portion of said first longitudinally extending side of said handle, a second side wall which overlies a portion of said second longitudinally extending side of said handle, a first corner portion which interconnects said first and second side walls of said sleeve and extends along said first corner portion of said handle, a third side wall which overlies a portion of said third longitudinally extending side of said handle, a second corner portion which interconnects said second and third side walls of said sleeve and extends along said second corner portion of said handle.

97. An apparatus for use in positioning a suture anchor in body tissue, said apparatus comprising a handle, said handle including surface means for at least partially defining a passage extending through said handle, a tubular inner member having a first end portion disposed in the passage in said handle and a second end portion spaced from said handle, said inner member having surface means defining a passage which extends axially through said inner member and is coaxial with the passage in said handle, a tubular outer member at least partially enclosing said inner member, said inner and outer members cooperating to form a chamber for receiving the anchor with a suture extending from the anchor through the passages in said handle and said inner member, said inner and outer members being relatively movable to eliminate the chamber and effect movement of the anchor into body tissue with the suture extending through the passages in said handle and said inner member, and an end cap which encloses an end portion of said handle, said end cap having an end surface which faces away from said second end portion of said inner member and is manually engageable to receive force which is transmitted through said handle to the anchor.

98. An apparatus as set forth in claim 97 wherein said end surface on said end cap has a configuration corresponding to the configuration of a portion of a sphere.

99. An apparatus as set forth in claim 97 wherein said handle has a triangular cross sectional configuration as viewed in a first plane extending through said handle in a direction perpendicular to a longitudinal central axis of said handle, said end surface on said end cap has a circular cross sectional configuration as viewed in a second plane extending through said end cap in a direction parallel to said first plane.

100. An apparatus as set forth in claim 97 wherein said handle has a first longitudinally extending side, said first longitudinally extending side of said handle having first and second longitudinally extending edge portions, said handle having a second longitudinally extending side, said second longitudinally extending side of said handle having first and second longitudinally extending edge portions, said first longitudinally extending edge portion of said second side of said handle being connected with said second longitudinally extending edge portion of said first side of said handle to form a first corner portion of said handle, said handle having a third longitudinally extending side, said third longitudinally extending side of said handle having first and second longitudinally extending edge portions, said first longitudinally extending edge portion of said third side of said handle being connected with said second longitudinally extending edge portion of said second side of said handle to form a second corner portion of said handle, said second longitudinally extending edge portion of said third side of said handle being connected with said first longitudinally extending edge portion of said first side of said handle to form a third corner portion of said handle, said first, second and third sides of said handle being at least partially enclosed by said end cap.

101. An apparatus as set forth in claim 100 wherein said first longitudinally extending side of said handle includes surface means for defining a first plurality of ribs which extend across said first longitudinally extending side of said handle between said first and third corner portions of said first longitudinally extending side of said handle, said first plurality of ribs being engageable by a thumb on a hand of a person manually gripping said handle, said third longitudinally extending side of said handle includes surface means for defining a second plurality of ribs which extend across said third longitudinally extending side of said handle between said second and third corner portions of said third longitudinally extending side of said handle, said second plurality of ribs being engageable by a finger on the hand of the person manually gripping said handle.

102. An apparatus as set forth in claim 101 wherein said second longitudinally extending side of said handle includes surface means for defining an elongated recess having a central axis which extends parallel to a longitudinal central axis of said second longitudinally extending side of said handle, said elongated recess being engageable by a finger on the hand of the person manually gripping said handle.

103. An apparatus as set forth in claim 102 wherein said second longitudinally extending side of said handle includes surface means for defining a third plurality of ribs which extend across said second longitudinally extending side of said handle between said first and second corner portions, in a direction transverse to the longitudinal central axis of said second longitudinally extending side of said handle, said elongated recess having a first and second end portions, said first end portion of said elongated recess being disposed closer to an end of said handle from which said shaft portion extends than said second end port ion of said elongated recess, said third plurality of ribs being disposed adjacent to said first end portion of said elongated recess.

104. An apparatus as set forth in claim 97 further including an actuator disposed on said handle, said actuator being movable relative to said handle by a finger on the hand of a person manually gripping the handle, said actuator being movable between a first position in which said inner and outer members are held against relative movement and a second position in which said inner and outer members are relatively movable.

105. An apparatus as set forth in claim 97 wherein said end cap includes surface means for defining an annular recess which receives a portion of the suture.

106. An apparatus for use in positioning a suture anchor in body tissue, said apparatus comprising a handle, said handle including surface means for at least partially defining a passage extending through said handle, a tubular inner member having a first end portion disposed in the passage in said handle and a second end portion spaced from said handle, said inner member having surface means defining a passage which extends axially through said inner member and is coaxial with the passage in said handle, and a tubular outer member at least partially enclosing said inner member, said inner and outer members cooperating to form a chamber for receiving the anchor with a suture extending from the anchor through the passages in said handle and said inner member, said inner and outer members being relatively movable to eliminate the chamber and effect movement of the anchor into body tissue with the suture extending through the passages in said handle and said inner member, said handle includes three longitudinally extending sides disposed in a triangular array, said three longitudinally extending sides of said handle being generally parallel to a central axis of the passage in said handle.

107. An apparatus as set forth in claim 106 wherein a first side of said three longitudinally extending sides includes surface means for defining a first plurality of ribs which extend across said first side of said handle in a direction transverse to a longitudinal central axis of said first side of said handle, a second side of said three longitudinally extending sides includes surface means for defining a second plurality of ribs which extend across said second side of said handle in a direction transverse to a longitudinal central axis of said second side of said handle.

108. An apparatus as set forth in claim 106 further including an actuator disposed on said handle, said actuator being movable relative to said handle by a person manually gripping the handle, said actuator being movable between a first position in which said inner and outer members are held against relative movement and a second position in which said inner and outer members are relatively movable.

109. An apparatus as set forth in claim 106 wherein an axially inner end portion of said inner member is fixedly connected with said handle, said outer member is slidable along said inner member to move said outer member between an extended position in which an axially outer end portion of said outer member extends beyond an axially outer end portion of said inner member and a retracted position in which said axially outer end portion of said inner member extends beyond said axially outer end portion of said outer member.

110. An apparatus as set forth in claim 106 wherein an axially outer end portion of said one of said inner and outer members has surface means for engaging body tissue and transmitting force between the body tissue and said one of said inner and outer members to effect movement of said one of said inner and outer members relative to said other of said inner and outer members.

111. An apparatus as set forth in claim 106 further including a stop member disposed on said handle and movable between a first stop position and a second stop position, said stop member being effective to limit movement of one of said inner and outer members relative to the other of said inner and outer members to a first distance when said stop member is in the first stop position of said stop member, said stop member being effective to limit movement of said one of said inner and outer members to a second distance when said stop member is in the second stop position of said stop member, said second distance being greater than said first distance.

112. An apparatus as set forth in claim 111 further including means movable relative to said handle to move said stop member between said first and second stop positions.

113. An apparatus as set forth in claim 111 further including indicia disposed on said handle for indicating when said stop member is in the first stop position and for indicating when said stop member is in the second stop position.

114. An apparatus as set forth in claim 106 wherein an axially outer end portion of said inner member has a curving configuration, said outer member having an axially outer end portion with a curving configuration corresponding to the curving configuration of said axially outer end portion of said inner member, at least a portion of the axially outer portion of said outer member being flexible to facilitate movement of said inner member relative to said outer member.

115. An apparatus as set forth in claim 106 wherein a first one of said longitudinally extending sides of said handle includes a slot which receives a portion of the suture, said slot in said handle being spaced from and extending parallel to the passage in said handle.

116. An apparatus as set forth in claim 115 wherein a second one of said longitudinally extending sides of said handle includes surface means for defining a recess for receiving a portion of the suture.

117. An apparatus as set forth in claim 116 wherein a third one of said longitudinally extending sides of said handle includes surface means for defining a recess which receives a needle connected with the suture.

118. An apparatus for use in positioning a suture anchor in body tissue, said apparatus comprising a handle, said handle including surface means for at least partially defining a passage extending through said handle, a tubular inner member having a first end portion disposed in the passage in said handle and a second end portion spaced from said handle, said inner member having surface means defining a passage which extends axially through said inner member and is coaxial with the passage in said handle, a tubular outer member at least partially enclosing said inner member, said inner and outer members cooperating to form a chamber for receiving the anchor with a suture extending from the anchor through the passages in said handle and said inner member, said inner and outer members being relatively movable to eliminate the chamber and effect movement of the anchor into body tissue with the suture extending through the passages in said handle and said inner member, and a retainer member disposed on said handle and movable relative to said handle between a retaining position in which said retainer member is effective to retain one of said inner and outer members against movement relative to the other of said inner and outer members and a release position in which said retainer member is ineffective to retain said one member against movement relative to said other member.

119. An apparatus as set forth in claim 118 wherein said retainer member has a surface which is manually engageable to move said retainer member from the retainer position to the release position with the anchor in the chamber formed by said inner and outer members and with the suture extending through the passages in said handle and said inner member.

120. An apparatus as set forth in claim 118 wherein the chamber defined by said inner and outer members receives only a trailing end portion of the anchor and a leading end portion of the anchor extends from the chamber when said retainer member is in the retaining position.

121. An apparatus as set forth in claim 118 wherein an axially outer end portion of said inner member is enclosed by said outer member when said retainer member is in the retaining position, said inner member and said outer member being movable relative to each other to a position in which said axially outer end portion of said inner member extends from said outer member when said retainer member is in the release position.

122. An apparatus as set forth in claim 118 wherein said retainer member has an opening with a first portion having a first configuration and a second portion having a second configuration, said retainer member being manually movable from the retaining position in which a central axis of said one of said inner and outer members extends through the first portion of the opening in said retainer member to the release position in which the central axis of said one of said inner and outer members extends through the second portion of the opening in said actuator to release said one of said inner and outer members for movement relative to the other of said inner and outer members.

123. An apparatus as set forth in claim 118 further including a guide surface disposed on said handle for guiding movement of said retainer member between the retaining position and the release position, said retainer member having a manually engageable surface against which force is manually applied to move said retainer member along said guide surface from the retaining position to the release position.

124. An apparatus as set forth in claim 118 wherein said first end portion of said inner member is fixedly connected with said handle, said outer member is said one of said inner and outer members and is slidable along said inner member to move said outer member from an extended position in which said outer member extends beyond said second end portion of said inner member to a retracted position in which said second end portion of said inner member extends beyond said outer member.

125. An apparatus as set forth in claim 118 wherein said one of said inner and outer members has surface means for engaging body tissue and transmitting force between the body tissue and said one of said inner and outer members to effect movement of said one of said inner and outer members relative to said other of said inner and outer members.

126. An apparatus as set forth in claim 118 wherein said handle includes surface means for defining a slot which extends between axially opposite end portions of said handle and which receives a portion of the suture.

127. An apparatus as set forth in claim 118 wherein said retainer member includes surface means for engaging a portion of a suture when said retainer member is in the retaining position to retain at least the portion of the suture engaged by said retainer member against movement relative to said handle.

128. An apparatus for use in positioning a suture anchor in body tissue, said apparatus comprising a handle, said handle including surface means for at least partially defining a passage extending through said handle, a tubular inner member having a first end portion disposed in the passage in said handle and a second end portion spaced from said handle, said inner member having surface means defining a passage which extends axially through said inner member and is coaxial with the passage in said handle, and a tubular outer member at least partially enclosing said inner member, said inner and outer members cooperating to form a chamber for receiving the anchor with a suture extending from the anchor through the passages in said handle and said inner member, said inner and outer members being relatively movable to eliminate the chamber and effect movement of the anchor into body tissue with the suture extending through the passages in said handle and said inner member, said first end portion of said tubular inner member is fixedly connected with said handle, said tubular outer member being movable axially along said tubular inner member between an extended position in which said tubular outer member extends axially into said handle for a first distance and a retracted position in which said tubular outer member extends axially into said handle for a second distance which is greater than said first distance.

129. An apparatus as set forth in claim 128 further including surface means connected with said tubular outer member for engaging body tissue and transmitting force between the body tissue and said tubular outer member to effect movement of said tubular outer member into said handle.

130. An apparatus as set forth in claim 128 further including means connected with said outer member for limiting the extent of movement of said outer member into said handle.

131. An apparatus as set forth in claim 128 further including a retainer member disposed on said handle and movable relative to said handle between a retaining position in which said retainer member is effective to retain said outer member in the extended position and a release position in which said retainer member is ineffective to retain said outer member in the extended position.

132. An apparatus as set forth in claim 131 wherein said retainer member includes surface means which is engageable with a portion of a suture connected with the anchor to retain the engaged portion of the suture against movement relative to said handle when said retainer member is in the retaining position.

133. An apparatus as set forth in claim 131 wherein said handle includes a guide surface along which said retainer member is movable between the retaining and release positions, said guide surface being effective to guide movement of the retainer member along a path having a central axis which extends transverse to a central axis of said outer member.

134. An apparatus as set forth in claim 131 wherein said retainer member has a manually engageable end portion against which force is manually applied to move said retainer member from the retaining position to the release position.

135. An apparatus as set forth in claim 131 further including first and second stop surfaces connected with said outer member, said first and second stop surfaces being spaced from each other along a central axis of said outer member, said retainer member being disposed adjacent to said first stop surface when said outer member is in the extended position, said retainer member being disposed adjacent to said second stop surface when said outer member is in the retracted position.

136. An apparatus as set forth in claim 131 wherein said retainer member includes an opening through which a central axis of said outer member extends, said opening being movable transversely to the central axis of said outer member upon movement of said retainer member between the retaining and release positions, the central axis of said outer member extends through a first portion of the opening in said retainer member when said retainer member is in the retaining position, the central axis of said outer member extends through a second portion of the opening in said retainer member when said retainer member is in the release position.

137. An apparatus as set forth in claim 131 wherein said handle includes three longitudinally extending sides disposed in a triangular array with longitudinal axes of said sides extending parallel to a central axis of said inner member, said retainer member projects from one of said sides of said handle when said retainer member is in the retaining position.

138. An apparatus as set forth in claim 128 wherein said handle includes three longitudinally extending sides disposed in a triangular array having a central axis which is parallel to central axes of said inner and outer members.

139. An apparatus as set forth in claim 128 wherein said chamber has a maximum axial extent when said outer member is in the extended position, said chamber having an axial extent which is less than the axial extent of the suture anchor when said outer member is in the extended position, said second end portion of said inner member cooperates with said outer member to form an end of said chamber which is engageable by a trailing end of the suture anchor when the suture anchor is in said chamber with a leading end of the suture anchor outside of said chamber and with said outer member in the extended position.

140. An apparatus as set forth in claim 128 further including means for limiting the depth to which an anchor is to be inserted into body tissue to a selected one of a plurality of depths, said means for limiting the depth to which an anchor is to be inserted into body tissue includes means for limiting the distance which said outer member moves along said inner member from the extended position to the retracted position to a selected one of a plurality of distances.

141. An apparatus for use in positioning a suture anchor relative to body tissue, said apparatus comprising a handle, an inner member having a first end portion connected with said handle and a second end portion which is spaced from said handle, an outer member at least partially enclosing said inner member, said outer member having a first end portion connected with said handle and a second end portion which is spaced from said handle, one of said inner and outer members being movable relative to the other of said inner and outer members to insert the anchor into body tissue, means for limiting the depth to which the anchor is inserted into body tissue upon relative movement between said inner and outer members, said means for limiting the depth to which the anchor is inserted into body tissue includes means for limiting the distance which said inner and outer members are movable relative to each other to a selected one of a plurality of distances, and surface means connected with said outer member for engaging body tissue and transmitting force between the body tissue and said outer member to effect movement of said outer member along said inner member through the selected one of the plurality of distances.

142. An apparatus as set forth in claim 141 wherein said outer member is movable into said handle under the influence of force applied against said surface means by the body tissue, said means for limiting the distance which said inner and outer members are movable relative to each other is disposed on said handle and is effective to block movement of said outer member into said handle upon movement of said outer member along said inner member through the selected one of the plurality of distances.

143. An apparatus as set forth in claim 141 wherein said inner member is fixedly connected with said handle, said means for limiting the distance which said inner and outer members are movable relative to each other includes means for limiting movement of said outer member relative to said inner member and said handle.

144. An apparatus as set forth in claim 141 further including a retainer member movable relative to said handle and inner member between a retaining position in which said retainer member is effective to retain said inner and outer members against relative movement and a release position in which said retainer member is ineffective to retain said outer member against movement relative to said inner member under the influence of force applied against said surface means by the body tissue.

145. An apparatus as set forth in claim 141 wherein said surface means is disposed on an end of said outer member.

146. An apparatus as set forth in claim 141 wherein said handle includes three longitudinally extending sides disposed in a triangular array having a central axis which is parallel to a central axis of said inner member.

147. An apparatus for use in positioning a suture anchor relative to body tissue, said apparatus comprising a handle, an inner member having a first end portion connected with said handle and a second end portion which is spaced from said handle, an outer member at least partially enclosing said inner member, said outer member having a first end portion connected with said handle and a second end portion which is spaced from said handle, one of said inner and outer members being movable relative to the other of said inner and outer members to insert the anchor into body tissue, and means for limiting the depth to which the anchor is inserted into body tissue upon relative movement between said inner and outer members, said means for limiting the depth to which the anchor is inserted into body tissue includes means for limiting the distance which said inner and outer members are movable relative to each other to a selected one of a plurality of distances, said means for limiting the depth to which the suture anchor is inserted into body tissue includes a stop member which is movable relative to said handle to a selected one of a plurality of positions which are located at different distances from said second end portions of said inner and outer members, said stop member being effective to block relative movement between said inner and outer members when said inner and outer members have moved relative to each other through the selected one of the plurality of distances.

148. An apparatus as set forth in claim 147 wherein said means for limiting the distance which said inner and outer members are movable relative to each other includes a stop surface which is fixedly connected with said one of said inner and outer members and is movable relative to the other of said inner and outer members, said stop member being engageable with said stop surface to limit movement of said one of said inner and outer members relative to the other of said inner and outer members.

149. An apparatus as set forth in claim 147 further including a retainer member movable relative to said handle between a retaining position in which said retainer member is effective to retain said inner and outer members against relative movement and a release position in which said retainer member is ineffective to retain said one of said inner and outer members against movement relative to the other of said inner and outer members.

150. An apparatus as set forth in claim 147 wherein said handle includes three longitudinally extending sides disposed in a triangular array having a central axis which is parallel to central axes of said inner and outer members, said stop member being movable along the central axis of the triangular array of longitudinally extending sides to vary the depth to which the suture anchor is inserted into the body tissue.

151. An apparatus as set forth in claim 147 further including indicator means connected with said stop member for indicating which one of the plurality of positions said stop member is located.

152. An apparatus as set forth in claim 147 further including an array of indications disposed on said handle with each of said indications corresponding to one of said plurality of positions of said stop member, and manually operable actuator means connected with said stop member and movable along said array of indications to move said stop member to the selected one of the plurality of positions.

153. An apparatus for use in positioning a suture anchor relative to body tissue, said apparatus comprising a handle, an inner member having a first end portion connected with said handle and a second end portion which is spaced from said handle, an outer member at least partially enclosing said inner member, said outer member having a first end portion connected with said handle and a second end portion which is spaced from said handle, one of said inner and outer members being movable relative to the other of said inner and outer members to insert the anchor into body tissue, and means for limiting the depth to which the anchor is inserted into body tissue upon relative movement between said inner and outer members, said means for limiting the depth to which the anchor is inserted into body tissue includes means for limiting the distance which said inner and outer members are movable relative to each other to a selected one of a plurality of distances, said means for limiting the depth to which the anchor is inserted into body tissue is at least partially disposed in said handle and includes a member which is manually movable along said handle to select a desired depth of insertion of the anchor into body tissue.

154. An apparatus as set forth in claim 153 further including a retainer member at least partially disposed in said handle, said retainer member being manually movable relative to said handle between a first position in which said one of said inner and outer members is retained against movement relative to the other of said inner and outer members and a second position in which said one of said inner and outer members is movable relative to the other of said inner and outer members.

155. An apparatus as set forth in claim 153 wherein said handle includes three longitudinally extending sides disposed in a triangular array having a central axis, said member being movable along the central axis of said triangular array of longitudinally extending sides to select a desired depth of insertion of the anchor into body tissue.

156. An apparatus as set forth in claim 153 further including indicator means for indicating the selected depth of insertion of the anchor into body tissue, said indicator means includes indicia disposed on said handle to indicate various depths of insertion of the anchor into body tissue and means connected with said member and movable with said member relative to said handle for cooperating with said indicia to indicate the position of said member relative to said handle.

157. An apparatus as set forth in claim 153 wherein said means for limiting the distance which said inner and outer members are movable relative to each other includes a stop surface which is fixedly connected with said one of said inner and outer members and is movable relative to the other of said inner and outer members.

158. An apparatus for use in positioning a suture anchor relative to body tissue, said apparatus comprising a handle, an inner member having a first end portion connected with said handle and a second end portion which is spaced from said handle, an outer member at least partially enclosing said inner member, said outer member having a first end portion connected with said handle and a second end portion which is spaced from said handle, one of said inner and outer members being movable relative to the other of said inner and outer members to insert the anchor into body tissue, and means for limiting the depth to which the anchor is inserted into body tissue upon relative movement between said inner and outer members, said means for limiting the depth to which the anchor is inserted into body tissue includes means for limiting the distance which said inner and outer members are movable relative to each other to a selected one of a plurality of distances, and said means for limiting the depth to which the anchor is inserted into body tissue includes a depth control member which is movable along one of said inner and outer members to a selected one of a plurality of positions which correspond to different depths of insertion of the anchor into body tissue.

159. An apparatus as set forth in claim 158 wherein said inner member is fixedly connected to said handle and said outer member is movable relative to said inner member, said depth control member being movable relative to said handle to a selected one of a plurality of positions, said depth control member being effective to block movement of said outer member relative to said inner member when said outer member has moved relative to said inner member through a distance corresponding to a desired depth of insertion of the anchor into body tissue.

160. An apparatus as set forth in claim 158 further including indicator means connected with said depth control member for indicating which one of the plurality of positions said depth control member is located.

161. An apparatus as set forth in claim 158 further including an array of indications disposed on said handle with each of said indications corresponding to one of said plurality of positions of said depth control member, and manually operable actuator means connected with said depth control member and movable along said array of indications to move said depth control member to the selected one of the plurality of positions.

162. An apparatus as set forth in claim 158 wherein said depth control member is at least partially disposed in said handle and is manually movable along said handle.

163. An apparatus as set forth in claim 162 further including an retainer member connected with said handle, said retainer member being movable relative to said handle between a first position in which said one of said inner and outer members is retained against movement relative to the other of said inner and outer members and a second position in which said one of said inner and outer members is movable relative to the other of said inner and outer members.

164. An apparatus as set forth in claim 158 wherein said inner and outer members cooperate to at least partially define a chamber which receives at least a portion of the anchor when said inner and outer members are in an initial position relative to each other, said inner member extends from said outer member for a distance which corresponds a desired depth of insertion of the anchor into body tissue when said one of said inner and outer members has been moved relative to the other of said inner and outer members through the selected one of the plurality of distances.

165. An apparatus as set forth in claim 158 wherein said first end portion of said inner member is fixedly connected with said handle, said outer member is said one of said inner and outer members, said means for limiting the distance which said inner and outer members are movable relative to each other to a selected one of a plurality of distances is effective to limit the distance which said outer member is movable relative to said inner member to the selected one of the plurality of distances.

166. An apparatus as set forth in claim 165 wherein said means for limiting the distance which said inner and outer members are movable relative to each other includes a stop surface which is fixedly connected with said outer member, said stop surface being disposed in engagement with said depth control member when said outer member has moved relative to said inner member through a distance corresponding to a desired depth of insertion of the anchor into body tissue.

167. An apparatus for use in positioning a suture anchor relative to body tissue, said apparatus comprising a handle, an inner member having a first end portion connected with said handle and a second end portion which is spaced from said handle, an outer member at least partially enclosing said inner member, said outer member having a first end portion connected with said handle and a second end portion which is spaced from said handle, one of said inner and outer members being movable relative to the other of said inner and outer members to insert the anchor into body tissue, means for limiting the depth to which the anchor is inserted into body tissue upon relative movement between said inner and outer members, said means for limiting the depth to which the anchor is inserted into body tissue includes means for limiting the distance which said inner and outer members are movable relative to each other to a selected one of a plurality of distances, and an actuator connected with said handle, said actuator being movable relative to said handle between a first position in which said one of said inner and outer members is retained against movement relative to the other of said inner and outer members and a second position in which said one of said inner and outer members is movable relative to the other of said inner and outer members.

168. An apparatus for use in positioning a suture anchor relative to body tissue, said apparatus comprising a handle, an inner member having a first end portion connected with said handle and a second end portion which is spaced from said handle, an outer member at least partially enclosing said inner member, said outer member having a first end portion connected with said handle and a second end portion which is spaced from said handle, one of said inner and outer members being movable relative to the other of said inner and outer members to insert the anchor into body tissue, and means for limiting the depth to which the anchor is inserted into body tissue upon relative movement between said inner and outer members, said means for limiting the depth to which the anchor is inserted into body tissue includes means for limiting the distance which said inner and outer members are movable relative to each other to a selected one of a plurality of distances, said inner and outer members cooperate to at least partially define a chamber which receives at least a portion of the anchor when said inner and outer members are in an initial position relative to each other, said inner member extends from said outer member for a distance which corresponds a desired depth of insertion of the anchor into body tissue when said one of said inner and outer members has been moved relative to the other of said inner and outer members through the selected one of the plurality of distances.

169. An apparatus for use in positioning a suture anchor relative to body tissue, said apparatus comprising a handle, an inner member having a first end portion connected with said handle and a second end portion which is spaced from said handle, an outer member at least partially enclosing said inner member, said outer member having a first end portion connected with said handle and a second end portion which is spaced from said handle, one of said inner and outer members being movable relative to the other of said inner and outer members to insert the anchor into body tissue, and means for limiting the depth to which the anchor is inserted into body tissue upon relative movement between said inner and outer members, said means for limiting the depth to which the anchor is inserted into body tissue includes means for limiting the distance which said inner and outer members are movable relative to each other to a selected one of a plurality of distances, said first end portion of said inner member is fixedly connected with said handle, said outer member is said one of said inner and outer members, said means for limiting the distance which said inner and outer members are movable relative to each other to a selected one of a plurality of distances is effective to limit the distance which said outer member is movable relative to said inner member to the selected one of the plurality of distances.

170. A method of positioning a suture anchor in body tissue, said method comprising the steps of positioning the anchor in a chamber formed between inner and outer members connected with a handle, retaining said inner and outer members against movement relative to the handle, manually moving an actuator member relative to the handle to release one of the inner and outer members for movement relative to the handle, and thereafter, moving the anchor relative to the body tissue while moving the one of the inner and outer members relative to the handle, said step of moving the anchor relative to the body tissue while moving the one of the inner and outer members relative to the handle includes moving the outer member into the handle.

171. A method as set forth in claim 170 wherein said step of moving the anchor relative to the body tissue while moving the one of the inner and outer members relative to the handle further includes moving the anchor under the influence of force transmitted from the handle through the inner member to the anchor.

172. A method as set forth in claim 170 further including the step of moving a leading end portion of the anchor into engagement with body tissue prior to performance of said step of manually moving an actuator member relative to the handle and while performing said step of retaining said inner and outer members against movement relative to the handle.

173. A method as set forth in claim 170 further including the said step of tensioning a suture extending through the anchor while retaining the inner and outer members against movement relative to the handle.

174. A method as set forth in claim 173 wherein said step of tensioning the suture includes gripping a portion of the suture with the actuator member.

175. A method as set forth in claim 170 wherein said step of moving the outer member into the handle includes moving the outer member relative to the handle from a first position in which the outer member extends a first distance into the handle to a second position in which the outer member extends a second distance into the handle, the second distance being greater than the first distance.

176. A method as set forth in claim 170 wherein said step of moving the anchor relative to the body tissue while moving the one of the inner and outer members relative to the handle includes maintaining a suture which extends through the anchor stationary relative to the handle.

177. A method as set forth in claim 170 further including pressing a trailing end of the anchor against an outer end of the inner member under the influence of force transmitted to the anchor through a suture while retaining the inner and outer members against movement relative to the handle.

178. A method as set forth in claim 170 further including th e steps of selecting a desired depth of insertion of the anchor into body tissue and interrupting said step of moving one of the inner and outer members relative to the handle upon insertion of the anchor to the desired depth in body tissue.

179. A method as set forth in claim 170 further including the step of moving a depth control member along the handle to a position which corresponds to a desired depth of insertion of the anchor into body tissue, said step of moving a depth control member along the handle being performed while retaining said inner and outer members against movement relative to the handle and prior to performance of said step of manually moving the actuator member relative to the handle.

180. An apparatus as set forth in claim 170 wherein said step of moving the outer member into the handle is performed while maintaining the inner member stationary relative to the handle.

181. An apparatus as set forth in claim 170 wherein said step of moving the outer member into the handle is performed under the influence of force applied against the outer member by the body tissue.

182. An apparatus as set forth in claim 170 wherein said step of moving the outer member into the handle includes sliding a surface on the outer member along a surface on the inner member.

183. A method of positioning a suture anchor in body tissue, said method comprising the steps of positioning the anchor in a chamber formed between inner and outer members connected with a handle, retaining said inner and outer members against movement relative to the handle, manually moving an actuator member relative to the handle to release one of the inner and outer members for movement relative to the handle, thereafter, moving the anchor relative to the body tissue while moving the one of the inner and outer members relative to the handle, and tensioning a suture extending through the anchor while retaining the inner and outer members against movement relative to the handle.

184. An apparatus as set forth in claim 183 further including the step of pressing an end portion of the anchor against an end portion of the inner member under the influence of force transmitted through the suture to the anchor during performance of said step of tensioning the suture.

185. A method as set forth in claim 183 wherein said step of moving the anchor relative to the body tissue while moving the one of the inner and outer members relative to the handle includes moving the outer member relative to the inner member in a direction toward the handle.

186. A method as set forth in claim 183 wherein said step of moving the anchor relative to the body tissue while moving the one of the inner and outer members relative to the handle includes moving the anchor under the influence of force transmitted from the handle through the inner member to the anchor.

187. A method as set forth in claim 183 further including the step of moving a leading end portion of the anchor into engagement with body tissue prior to performance of said step of manually moving an actuator member relative to the handle and while performing said step of retaining said inner and outer members against movement relative to the handle.

188. A method as set forth in claim 183 wherein said step of tensioning a suture extending through the anchor while retaining the inner and outer members against movement relative to the handle includes tensioning a first portion of the suture which extends away from the anchor through the handle and tensioning a second portion of the suture which extends along an outer side surface of the outer member.

189. A method as set forth in claim 183 wherein said step of tensioning the suture includes gripping a portion of the suture with the actuator member.

190. A method as set forth in claim 183 wherein said step of moving the anchor relative to the body tissue while moving the one of the inner and outer members relative to the handle includes moving the outer member relative to the handle from a first position in which the outer member extends a first distance into the handle to a second position in which the outer member extends a second distance into the handle, the second distance being greater than the first distance.

191. A method as set forth in claim 183 wherein said step of moving the anchor relative to the body tissue while moving the one of the inner and outer members relative to the handle includes maintaining the suture which extends through the anchor stationary relative to the handle.

192. A method as set forth in claim 183 further including pressing a trailing end of the anchor against an outer end of the inner member under the influence of force transmitted to the anchor through a suture while retaining the inner and outer members against movement relative to the handle.

193. A method as set forth in claim 183 further including the steps of selecting a desired depth of insertion of the anchor into body tissue and interrupting said step of moving one of the inner and outer members relative to the handle upon insertion of the anchor to the desired depth in body tissue.

194. A method as set forth in claim 183 further including the step of moving a depth control member along the handle to a position which corresponds to a desired depth of insertion of the anchor into body tissue, said step of moving a depth control member along the handle being performed while retaining said inner and outer members against movement relative to the handle and prior to performance of said step of manually moving the actuator member relative to the handle.

195. A method of positioning a suture anchor in body tissue, said method comprising the steps of positioning the anchor in a chamber formed between inner and outer members connected with a handle, retaining said inner and outer members against movement relative to the handle, manually moving an actuator member relative to the handle to release one of the inner and outer members for movement relative to the handle, and thereafter, moving the anchor relative to the body tissue while moving the one of the inner and outer members relative to the handle, said step of moving the anchor relative to the body tissue while moving the one of the inner and outer members relative to the handle includes moving the outer member relative to the handle from a first position in which the outer member extends a first distance into the handle to a second position in which the outer member extends a second distance into the handle, the second distance being greater than the first distance.

196. A method of positioning a suture anchor in body tissue, said method comprising the steps of positioning the anchor in a chamber formed between inner and outer members connected with a handle, retaining said inner and outer members against movement relative to the handle, manually moving an actuator member relative to the handle to release one of the inner and outer members for movement relative to the handle, and thereafter, moving the anchor relative to the body tissue while moving the one of the inner and outer members relative to the handle, step of moving the anchor relative to the body tissue while moving the one of the inner and outer members relative to the handle includes maintaining a suture which extends through the anchor stationary relative to the handle.

197. A method as set forth in claim 196 further including pressing a trailing end of the anchor against an outer end of the inner member under the influence of force transmitted to the anchor through a suture while retaining the inner and outer members against movement relative to the handle.

198. A method as set forth in claim 196 wherein said step of moving the anchor relative to the body tissue while moving the one of the inner and outer members relative to the handle includes moving the outer member relative to the inner member and the suture in a direction toward the handle.

199. A method as set forth in claim 196 wherein said step of moving the anchor relative to the body tissue while moving the one of the inner and outer members relative to the handle includes moving the anchor under the influence of force transmitted from the handle through the inner member to the anchor.

200. A method as set forth in claim 196 further including the step of moving a leading end portion of the anchor into engagement with body tissue prior to performance of said step of manually moving an actuator member relative to the handle and while performing said steps of retaining said inner and outer members against movement relative to the handle and maintaining the suture stationary relative to the handle.

201. A method as set forth in claim 196 further including the step of tensioning a suture extending through the anchor while retaining the inner and outer members against movement relative to the handle.

202. A method as set forth in claim 196 wherein said step of maintaining the suture stationary relative to the handle includes gripping a portion of the suture with the actuator member.

203. A method as set forth in claim 196 wherein said step of moving the anchor relative to the body tissue while moving the one of the inner and outer members relative to the handle includes moving the outer member relative to the handle from a first position in which the outer member extends a first distance into the handle to a second position in which the outer member extends a second distance into the handle, the second distance being greater than the first distance.

204. A method of positioning a suture anchor in body tissue, said method comprising the steps of positioning the anchor in a chamber formed between inner and outer members connected with a handle, retaining said inner and outer members against movement relative to the handle, manually moving an actuator member relative to the handle to release one of the inner and outer members for movement relative to the handle, thereafter, moving the anchor relative to the body tissue while moving the one of the inner and outer members relative to the handle, and pressing a trailing end of the anchor against an outer end of the inner member under the influence of force transmitted to the anchor through a suture while retaining the inner and outer members against movement relative to the handle.

205. A method as set forth in claim 204 wherein said step of moving the anchor relative to the body tissue while moving the one of the inner and outer members relative to the handle includes moving the outer member relative to the inner member while continuing to press the trailing end of the anchor against the outer end of the inner member.

206. A method as set forth in claim 204 wherein said step of moving the anchor relative to the body tissue while moving the one of the inner and outer members relative to the handle includes moving the anchor relative to the body tissue under the influence of force transmitted from the handle through the inner member to the anchor.

207. A method as set forth in claim 204 further including the steps of selecting a desired depth of insertion of the anchor into body tissue and interrupting said step of moving one of the inner and outer members relative to the handle upon insertion of the anchor to the desired depth in body tissue.

208. A method as set forth in claim 204 further including the step of moving a depth control member along the handle to a position which corresponds to a desired depth of insertion of the anchor into body tissue, said step of moving a depth control member along the handle being performed while retaining said inner and outer members against movement relative to the handle and prior to performance of said step of manually moving the actuator member relative to the handle.

209. A method of positioning a suture anchor relative to body tissue, said method comprising the steps of moving an inner member and a tubular outer member toward body tissue with a leading end portion of the anchor extending from the outer member and with the outer member enclosing a trailing end portion of the anchor and a portion of inner member, engaging body tissue with the leading end portion of the anchor while the trailing end portion of the anchor is enclosed by the outer member, said step of moving an inner member and an outer member toward body tissue and said step of engaging body tissue with the leading end portion of the anchor being performed with the anchor stationary relative to the inner and outer members, thereafter, moving the anchor and inner member relative to the outer member to position the anchor relative to the body tissue, said step of moving an inner member and an outer member toward body tissue and said step of engaging body tissue with the leading end portion of the anchor are performed with a retainer member in a first position in which the retainer member is effective to retain said inner member and said outer member against movement relative to each other, and moving the retainer member from the first position to a second position in which the retainer member is ineffective to retain said inner member and said outer member against movement relative to each other, said step of moving the anchor and inner member relative to the outer member being performed with the retainer member in the second position.

210. A method as set forth in claim 209 further including the steps of selecting a desired depth of insertion of the anchor into body tissue and interrupting said step of moving the anchor and inner member relative to the outer member upon insertion of the anchor to the desired depth in the body tissue.

211. A method as set forth in claim 209 further including the steps of moving a stop member along the inner member to a position which corresponds to a desired depth of insertion of the anchor into body tissue, and blocking movement of the anchor and inner member relative to the outer member with the stop member upon insertion of the anchor to the desired depth into body tissue.

212. A method of positioning a suture anchor relative to body tissue, said method comprising the steps of moving an inner member and a tubular outer member toward body tissue with a leading end portion of the anchor extending from the outer member and with the outer member enclosing a trailing end portion of the anchor and a portion of inner member, engaging body tissue with the leading end portion of the anchor while the trailing end portion of the anchor is enclosed by the outer member, said step of moving an inner member and an outer member toward body tissue and said step of engaging body tissue with the leading end portion of the anchor being performed with the anchor stationary relative to the inner and outer members, thereafter, moving the anchor and inner member relative to the outer member to position the anchor relative to the body tissue, moving a stop member along the inner member to a position which corresponds to a desired depth of insertion of the anchor into body tissue, and blocking movement of the anchor and inner member relative to the outer member with the stop member upon insertion of the anchor to the desired depth into body tissue.

213. A method positioning a suture anchor relative to body tissue, said method comprising the steps of manually positioning a depth control member relative to a handle to select an anchor insertion depth, said step of manually positioning a depth control member relative to a handle includes moving the depth control member along an opening in the handle to a position corresponding to a desired depth of insertion of the anchor into body tissue, moving the anchor into body tissue by transmitting force from the handle through an inner member to the anchor while the inner member is at least partially enclosed by an outer member, said step of moving the anchor into body tissue includes moving the outer member relative to the inner member under the influence of force applied against the outer member by the body tissue, and blocking movement of the outer member relative to the inner member upon insertion of the anchor into the body tissue to a depth corresponding to the position of the depth control member relative to the handle.

214. A method positioning a suture anchor relative to body tissue, said method comprising the steps of manually positioning a depth control member relative to a handle to select an anchor insertion depth, said step of manually positioning control member relative to a handle includes sliding the depth control member along the inner member to a position corresponding to a desired depth of insertion of the anchor into body tissue, moving the anchor into body tissue by transmitting force from the handle through an inner member to the anchor while the inner member is at least partially enclosed by an outer member, said step of moving the anchor into body tissue includes moving the outer member relative to the inner member under the influence of force applied against the outer member by the body tissue, and blocking movement of the outer member relative to the inner member upon insertion of the anchor into the body tissue to a depth corresponding to the position of the depth control member relative to the handle.

215. A method as set forth in claim 214 wherein said step of sliding the depth control member along the inner member is performed with the depth control member at least partially enclosed by the handle.

216. A method as set forth in claim 214 wherein said step of blocking movement of the outer member relative to the inner member includes blocking movement of the outer member with the depth control member.

217. A method as set forth in claim 214 wherein said step of moving the outer member relative to the inner member includes retracting the outer member into the handle.

218. A method positioning a suture anchor relative to body tissue, said method comprising the steps of manually positioning a depth control member relative to a handle to select an anchor insertion depth, moving the anchor into body tissue by transmitting force from the handle through an inner member to the anchor while the inner member is at least partially enclosed by an outer member, said step of moving the anchor into body tissue includes moving the outer member relative to the inner member under the influence of force applied against the outer member by the body tissue, and blocking movement of the outer member relative to the inner member upon insertion of the anchor into the body tissue to a depth corresponding to the position of the depth control member relative to the handle, said step of blocking movement of the outer member relative to the inner member includes blocking movement of the outer member with the depth control member.

219. A method as set forth in claim 218 wherein said step of manually positioning a depth control member relative to a handle includes moving the depth control member along an opening in the handle to a position corresponding to a desired depth of insertion of the anchor into body tissue.

220. A method as set forth in claim 218 wherein said step of manually positioning control member relative to a handle includes sliding the depth control member along the inner member to a position corresponding to a desired depth of insertion of the anchor into body tissue.

221. A method as set forth in claim 220 wherein said step of sliding the depth control member along the inner member is performed with the depth control member at least partially enclosed by the handle.

222. A method as set forth in claim 218 wherein said step of moving the outer member relative to the inner member includes retracting the outer member into the handle.

223. A method positioning a suture anchor relative to body tissue, said method comprising the steps of manually positioning a depth control member relative to a handle to select an anchor insertion depth, moving the anchor into body tissue by transmitting force from the handle through an inner member to the anchor while the inner member is at least partially enclosed by an outer member, said step of moving the anchor into body tissue includes moving the outer member relative to the inner member under the influence of force applied against the outer member by the body tissue, said step of moving the outer member relative to the inner member includes retracting the outer member into the handle, and blocking movement of the outer member relative to the inner member upon insertion of the anchor into the body tissue to a depth corresponding to the position of the depth control member relative to the handle.

224. A method of positioning a suture anchor relative to body tissue, said method comprising the steps of moving an anchor toward an imperforate surface on body tissue, perforating the imperforate surface on the body tissue with a leading end portion of the anchor to form an opening in the surface of the body tissue, said step of perforating an imperforate surface on the body tissue with a leading end portion of the anchor being performed with a suture extending through a central passage in the anchor and across the leading end portion of the anchor, and thereafter, moving the anchor through the opening into the body tissue.

225. A method as set forth in claim 224 wherein said step of moving an inner member and a tubular outer member toward the body tissue and perforating the imperforate surface on the body tissue are performed with a retainer member in a first position in which the retainer member is effective to retain said inner member and said tubular outer member against movement relative to each other, said method further including moving the retainer member from the first position to a second position in which the retainer member is ineffective to retain said inner member and said tubular outer member against movement relative to each other, and positioning the anchor relative to the body tissue while the retainer member is in the second position.

226. A method as set forth in claim 224 further wherein said step of perforating the imperforate surface on the body tissue includes moving the anchor and an inner member into the body tissue under the influence of force transmitted from a handle through the inner member to a trailing end of the anchor while retracting an outer member toward the handle and maintaining the inner member stationary relative to the handle.

227. A method as set forth in claim 224 wherein said step of perforating the imperforate surface on the body tissue includes retracting an outer member under the influence of force applied against the outer member by the body tissue by sliding the outer member along an outer side surface of an inner member which is at least partially enclosed by the outer member.

228. A method of positioning a suture anchor relative to body tissue, said method comprising the steps of moving an anchor toward an imperforate surface on body tissue, perforating the imperforate surface on the body tissue with a leading end portion of the anchor to form an opening in the surface of the body tissue, and thereafter, moving the anchor through the opening into the body tissue, said step of moving the anchor toward an imperforate surface on body tissue includes moving an inner member and a tubular outer member toward the body tissue with the leading end portion of the anchor extending from the outer member and with the inner member disposed in engagement with a trailing end of the anchor, said steps of moving an inner member and a tubular outer member toward the body tissue and perforating the imperforate surface on the body tissue being performed with the anchor stationary relative to the inner member and tubular outer member, said method further including the step of moving the anchor and inner member relative to the tubular outer member to position the anchor relative to body tissue, said step of moving an inner member and a tubular outer member toward the body tissue and perforating the imperforate surface on the body tissue are performed with a retainer member in a first position in which the retainer member is effective to retain said inner member and said tubular outer member against movement relative to each other, said method further including moving the retainer member from the first position to a second position in which the retainer member is ineffective to retain said inner member and said tubular outer member against movement relative to each other, said step of moving the anchor and inner member relative to the tubular outer member being performed with the retainer member in the second position.

229. An apparatus for use in positioning a suture anchor relative to body tissue, said apparatus comprising a handle, an inner member, an outer member at least partially enclosing said inner member, at least one of said inner and outer members being connected with said handle, said inner and outer members being relatively movable to move the anchor relative to the body tissue, and retainer means connected with said handle and at least one of said inner and outer members for retaining said inner and outer members against movement relative to each other, said retainer means being manually operable from an engaged condition to a release condition to enable relative movement to occur between said inner and outer members.

230. An apparatus as set forth in claim 229 wherein said retainer means includes surface means for retaining at least a portion of a suture connected with the anchor against movement when said retainer means is in the engaged condition.

231. An apparatus as set forth in claim 229 wherein said outer member is movable relative to said handle and said inner member when said retainer means is in the release condition.

232. An apparatus as set forth in claim 229 wherein said retainer means includes first and second spaced apart surfaces connected with one of said inner and outer members and a retainer member, said retainer member being disposed adjacent to said first surface when said retainer means is in the engaged condition, said retainer member being disposed adjacent to said second surface after relative movement between said inner and outer members through a range of movement with said retainer means in the release condition.

233. An apparatus as set forth in claim 229 wherein said retainer means includes a member which is manually movable in a direction transverse to central axes of said inner and outer members to effect operation of said retainer means from the engaged condition to the release condition.

234. An apparatus as set forth in claim 229 further including depth control means for limiting the extent of relative movement between said inner and outer members when said retainer means is in the release condition to control the depth to which the suture anchor is inserted into body tissue, said depth control means being manually adjustable to vary the extent of relative movement between said inner and outer members to thereby vary the depth to which a suture anchor is inserted into body tissue.

235. An apparatus as set forth in claim 229 wherein said inner member has surface means for applying force to a trailing end of the suture anchor to move the suture anchor into body tissue during relative movement between said inner and outer members with said retainer means in the release condition.

236. An apparatus as set forth in claim 229 wherein said inner member has surface means for defining a passage which receives a suture which extends through the anchor, said passage in said inner member extends between opposite end portions of said inner member.

237. An apparatus as set forth in claim 229 further including surface means connected with said outer member for engaging body tissue and transmitting force between the body tissue and said outer member to effect relative movement between said inner and outer members when said retainer means is in the release condition.

238. An apparatus as set forth in claim 229 further including means for limiting the extent of relative movement between said inner and outer members when said retainer means is in the release condition.

239. An apparatus as set forth in claim 229 wherein said retainer means includes a retainer member disposed on said handle and movable relative to said handle between a first position in which said retainer means is in the engaged condition and a second position in which said retainer means is in the release condition.

240. An apparatus as set forth in claim 239 wherein said retainer member includes surface means which is engageable with a portion of a suture connected with the anchor to retain the engaged portion of the suture against movement relative to said handle when said retainer member is in the first position.

241. An apparatus as set forth in claim 239 wherein said handle includes a guide surface along which said retainer member is movable between the first and second positions, said guide surface being effective to guide movement of the retainer member along a path having a central axis which extends transverse to a central axis of said handle.

242. An apparatus as set forth in claim 239 wherein said retainer member has a manually engageable end portion against which force is manually applied to move said retainer member from the first position to the second position.

243. An apparatus as set forth in claim 239 further including first and second stop surfaces connected with one of said inner and outer members, said first and second stop surfaces being spaced from each other along a central axis of said handle, said retainer member being disposed adjacent to said first stop surface when said retainer means is in the engaged condition, said retainer member being disposed adjacent to said second stop surface when said retainer means is in the release condition and relative movement has occurred between said inner and outer members.

244. An apparatus as set forth in claim 239 wherein said retainer member includes an opening through which a central axis of at least one of said inner and outer members extends, said opening being movable transversely to the central axis of said one of said inner and outer members upon movement of said retainer member between the first and second positions, the central axis of said one of said inner and outer members extends through a first portion of the opening in said retainer member when said retainer member is in the first position, the central axis of said one of said inner and outer members extends through a second portion of the opening in said retainer member when said retainer member is in the second position.

245. An apparatus as set forth in claim 239 wherein said handle includes three longitudinally extending sides disposed in a triangular array, said retainer member projects from one of said sides of said handle when said retainer member is in the first position.

246. An apparatus as set forth in claim 229 wherein said handle includes three longitudinally extending sides disposed in a triangular array having a central axis which is parallel to a central axis of at least one of said inner and outer members.

247. An apparatus as set forth in claim 246 wherein a first one of said longitudinally extending sides of said handle includes surface means for defining a slot which receives a portion of a suture, said slot having a longitudinal central axis which extends parallel to a longitudinal central axis of at least one of said inner and outer members.

248. An apparatus as set forth in claim 247 wherein a second one of said longitudinally extending sides of said handle includes surface means for defining a recess which receives a needle connected with the suture.

249. An apparatus as set forth in claim 248 wherein a third one of said longitudinally extending sides of said handle includes surface means for defining a recess for receiving a portion of the suture.

250. An apparatus as set forth in claim 246 wherein said longitudinally extending sides of said handle are interconnected by a plurality of longitudinally extending corner portions having axes which extend parallel to the longitudinal central axis of said triangular array of longitudinally extending sides, a first one of said longitudinally extending sides of said handle including a first plurality of ribs which extend between a first one of said corner portions and a second one of said corner portions, a second one of said longitudinally extending sides of said handle including a second plurality of ribs which extend between said second one of said corner portions and a third one of said corner portions.

251. An apparatus for use in positioning a suture anchor relative to body tissue, said apparatus comprising a handle, a longitudinally extending inner member fixedly connected with and extending axially outward from said handle, a tubular outer member slidable along an axially extending outer side surface of said inner member, and a retainer member connected with said handle, said retainer member being manually movable relative to said handle between a first position in which said outer member is retained against movement in an axial direction along the outer side surface of said inner member and a second position in which said outer member is slidable in an axial direction along the outer side surface of said inner member, said inner and outer members cooperate to hold the suture anchor against movement relative to said handle when said retainer member is in the first position, at least one of said inner and outer members has a surface against which the suture anchor is pressed when said retainer member is in the first position.

252. An apparatus as set forth in claim 251 further including surface means connected with said handle for gripping at least a portion of the suture when said retainer member is in the first position and the suture anchor is pressed against the surface on one of said inner and outer members.

253. An apparatus as set forth in claim 251 further including first and second spaced apart surfaces connected with said outer member, said retainer member being disposed adjacent to said first surface when said retainer member is in the first position, said retainer member being disposed adjacent to said second surface after relative movement between said inner and outer members with said retainer member in the second position.

254. An apparatus as set forth in claim 251 wherein said retainer member is manually movable between the first and second positions in a direction transverse to a central axis of said inner member.

255. An apparatus as set forth in claim 251 further including depth control means for limiting the extent of relative movement between said inner and outer members when said retainer member is in the second position to control the depth to which the suture anchor is inserted into body tissue, said depth control means being manually adjustable to vary the extent of relative movement between said inner and outer members to thereby vary the depth to which a suture anchor is inserted into body tissue.

256. An apparatus as set forth in claim 251 wherein said inner member has surface means for defining a passage which receives a portion of the suture, said passage in said inner member extends between opposite end portions of said inner member.

257. An apparatus as set forth in claim 251 further including surface means connected with said outer member for engaging body tissue and transmitting force between the body tissue and said outer member to slide said outer member along the axially extending outer side surface of said inner member in a direction toward said handle when said retainer member is in the second position.

258. An apparatus as set forth in claim 251 further including means connected with said outer member for limiting the extent of sliding movement of said outer member along the outer side surface of said inner member when said retainer member is in the second position.

259. An apparatus as set forth in claim 251 wherein said retainer member includes surface means which is engageable with a portion of the suture to retain the engaged portion of the suture against movement relative to said handle when said retainer member is in the first position.

260. An apparatus as set forth in claim 251 further including a guide surface along which said retainer member is movable between the first and second positions, said guide surface being connected with said handle and being effective to guide movement of the retainer member along a path having a central axis which extends transverse to a central axis of said handle.

261. An apparatus as set forth in claim 251 wherein said retainer member has a manually engageable end portion against which force is manually applied to move said retainer member from the first position to the second position.

262. An apparatus as set forth in claim 251 further including first and second stop surfaces connected with said outer member, said first and second stop surfaces being spaced from each other along the central axis of said inner member, said retainer member being disposed adjacent to said first stop surface when said retainer member is in the first position, said retainer member being disposed adjacent to said second stop surface when said retainer member is in the second position.

263. An apparatus as set forth in claim 251 wherein said retainer member includes an opening through which a central axis of said outer member extends, said opening being movable transversely to the central axis of said outer member upon movement of said retainer member between the first and second positions, the central axis of said outer member extends through a first portion of the opening in said retainer member when said retainer member is in the first position, the central axis of said outer member extends through a second portion of the opening in said retainer member when said retainer member is in the second position.

264. An apparatus as set forth in claim 251 wherein said handle includes three longitudinally extending sides disposed in a triangular array with longitudinal axes of said sides extending parallel to a central axis of said inner member, said retainer member projects from one of said sides of said handle when said retainer member is in the first position.

265. An apparatus as set forth in claim 251 wherein said handle includes three longitudinally extending sides disposed in a triangular array having a central axis which is parallel to a central axis of said handle.

266. An apparatus as set forth in claim 265 wherein one of said longitudinally extending sides of said handle includes surface means for defining a slot which receives a portion of the suture.

267. An apparatus as set forth in claim 265 wherein one of said longitudinally extending sides of said handle includes surface means for defining a recess which receives a needle connected with the suture.

268. An apparatus as set forth in claim 265 wherein one of said longitudinally extending sides of said handle includes surface means for defining a recess for receiving a portion of the suture.

269. An apparatus as set forth in claim 265 wherein said longitudinally extending sides of said handle are interconnected by a plurality of longitudinally extending corner portions having axes which extend parallel to a longitudinal central axis of said inner member, a first one of said longitudinally extending sides of said handle including a first plurality of ribs which extend between a first one of said corner portions and a second one of said corner portions, a second one of said longitudinally extending sides of said handle including a second plurality of ribs which extend between said second one of said corner portions and a third one of said corner portions.

270. An apparatus as set forth in claim 251 further including means for limiting the depth to which an anchor is to be inserted into body tissue to a selected one of a plurality of depths, said means for limiting the depth to which an anchor is to be inserted into body tissue includes means for limiting the distance which said outer member slides along said outer side surface of said inner member to a selected one of a plurality of distances.

271. An apparatus as set forth in claim 270 wherein said means for limiting the depth to which an anchor is inserted into body tissue includes depth indicator means disposed on said handle for indicating the depth to which an anchor is to be inserted into body tissue.

272. An apparatus as set forth in claim 251 wherein said inner and outer members have a nonlinear longitudinal configuration, at least a portion of said outer member being flexible to accommodate movement of said outer member along a nonlinear portion of said inner member.

* * * * *

UNITED STATES PATENT AND TRADEMARK OFFICE
CERTIFICATE OF CORRECTION

PATENT NO : 5,782,862
DATED : July 21, 1998
INVENTOR(S) : Peter M. Bonutti

It is certified that error appears in the above-identified patent and that said Letters Patent are hereby corrected as shown below:

Col. 52, line 47
 replace "218"
 with --220--.

Signed and Sealed this

Third Day of April, 2001

Attest:

NICHOLAS P. GODICI

Attesting Officer

Acting Director of the United States Patent and Trademark Office